United States Patent [19]

Nakamura et al.

[11] Patent Number: 4,921,785
[45] Date of Patent: May 1, 1990

[54] SILVER HALIDE PHOTOGRAPHIC MATERIAL

[75] Inventors: Koki Nakamura; Ichizo Toya, both of Kanagawa, Japan

[73] Assignee: Fuji Photo Film Co., Ltd., Kanagawa, Japan

[21] Appl. No.: 188,562

[22] Filed: Apr. 29, 1988

[30] Foreign Application Priority Data

Apr. 30, 1987 [JP] Japan .................................. 62-106890

[51] Int. Cl.$^5$ ........................... G03C 1/30; G03C 1/04
[52] U.S. Cl. ..................................... 430/621; 430/622; 430/623; 430/624; 430/626; 430/642; 430/955
[58] Field of Search ............... 430/621, 622, 623, 624, 430/626, 642, 432

[56] References Cited

U.S. PATENT DOCUMENTS

| | | | |
|---|---|---|---|
| 4,028,320 | 6/1977 | Sera et al. | 430/622 |
| 4,096,137 | 6/1978 | Sera et al. | 430/642 |
| 4,543,324 | 9/1985 | Himmelmann | 430/622 |
| 4,783,396 | 11/1988 | Nakamura et al. | 430/623 |

Primary Examiner—Paul R. Michl
Assistant Examiner—Mark R. Buscher
Attorney, Agent, or Firm—Sughrue, Mion, Zinn, Macpeak & Seas

[57] ABSTRACT

A silver halide photographic material comprises a support having thereon at least one light-sensitive silver halide emulsion layer, at least one layer of said material comprising gelatin crosslinked with a crosslinking agent, said crosslinks being capable of being cleaved on reduction.

10 Claims, No Drawings

SILVER HALIDE PHOTOGRAPHIC MATERIAL

FIELD OF THE INVENTION

This invention concerns silver halide photographic materials, and more precisely silver halide photographic materials which have a high film strength during processing and good water washing properties.

BACKGROUND OF THE INVENTION

In general, the addition of large quantities of film hardening agents has been adopted for increasing the wet film strength during processing of silver halide photographic materials. However, it is known that the washing properties in the water washing process are adversely affected when the hardness of the film is increased in order to improve the wet film strength during processing, and the storage properties of the silver image deteriorate. Consequently, silver halide photographic materials which have a high wet film strength during processing and good washing properties during the water washing process are clearly desirable.

SUMMARY OF THE INVENTION

An object of this invention is to provide silver halide photographic materials which have a high wet strength during processing and good water washing properties.

It has been discovered that these and other objects of the invention are attained by a silver halide photographic material composed of a support having thereon, at least one light-sensitive silver halide emulsion layer, at least one layer of said material containing gelatin crosslinked with a crosslinking agent of the crosslinks capable of being cleaved on reduction thereof.

DETAILED DESCRIPTION OF THE INVENTION

Compounds represented by general formula (I) below are preferred crosslinking agents in the present invention:

$$PWR\text{-}[(Time)_t\text{-}(CG)_n]_p \atop | \atop (CG)_m \qquad (I)$$

In general formula (I), PWR represents a group capable of releasing $\text{-}[(Time)_t\text{-}(CG)_n]_p$ on reduction; CG represents a group capable of bonding with gelatin; n, m and p each is an integer of 1 to 3; and t is 0 or 1.

CG may be any group capable of forming covalent bonding with gelatin, and is preferably the groups represented by formulae (1) to (11), as set forth below.

$$-X^1-CO-CH_2Y^1 \qquad \text{Formula (1)}$$

wherein $X^1$ represents a single bond or $-O-$; and
$Y^1$ represents an electron withdrawing group, for example,

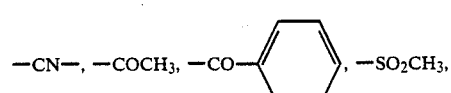
$-CN-$, $-COCH_3$, $-CO-$ , $-SO_2CH_3$,

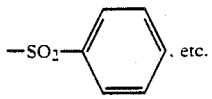
, etc.

$-SO_2CH=CH_2$      Formula (2)

$-SO_2CH_2CH_2X^2$      Formula (3)

wherein
$X^2$ represents a group released by substitution reaction or elimination reaction upon reacting the group of formula (3) with a nucleophilic reagent or group of formula (3) with a nucleophilic reagent or base, for example, $-Cl$, $-OSO_2CH_3$,

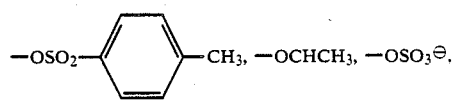
$-OSO_2-$〈 〉$-CH_3$, $-OCHCH_3$, $-OSO_3^{\ominus}$,

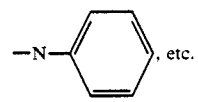
$-N-$ , etc.

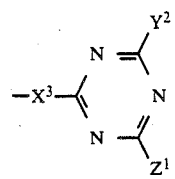
Formula (4)

wherein $X^3$ represents a single bond, $-O-$, $-N(R)-$ (wherein R represents hydrogen atom, alkyl group, and aralkyl group), $Y^2$ and $Z^1$ each represents halogen atom (such as Cl or Br), hydroxy group and salt thereof, substituted or unsubstituted amino group, provided that at least one of $Y^2$ and $Z^1$ is halogen atom.

$-CHO$      Formula (5)

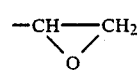
Formula (6)

$-NCO$      Formula (7)

$-NHCONHCOCH=CH_2$      Formula (8)

$-NHCONHCO-CH_2CH_2-X^2$      Formula (9)

wherein
$X^2$ means the same as defined in formula (3).

$-COX^4$      Formula (10)

wherein $X^4$ is a group capable of being easily released upon reacting a functional group in formula (10) with an amino group of gelatin, for example, $-Cl$,

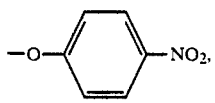

—O—CH$_2$, —CN, succinimido-1-yloxy group, 2-pyridyloxy group.

Formula (10) is known generally as active ester group or mixed acid anhydride.

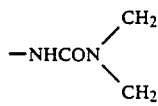  Formula (11)

PWR is described in greater detail below. PWR is a group which, on reduction, cleaves the single bond to —[(Time)$_t$—(CG)$_n$]$_p$, and it may be the moiety which contains an electron accepting center and an intramolecular nucleophilic substitution reaction center in a compound which releases a photographically useful reagent by means of an intramolecular nucleophilic substitution reaction following reduction, such as those disclosed in U.S. Pat. Nos. 4,139,389, 4,139,379 and 4,564,577 and in Japanese Patent Application (OPI) Nos. 185333/84 and 84453/82, or to the moiety which contains an electron accepting quinonoid center and a carbon atom which links this to a photographically useful reagent in a compound in which the photographically useful reagent is eliminated by an intramolecular electron transfer reaction, after reduction, such as those disclosed in U.S. Pat. No. 4,232,107, Japanese Patent Application (OPI) No. 101649/84, *Research Disclosure* (1984) (4) 24025, or in Japanese Patent Application (OPI) No. 88257/86 (the term "OPI" as used herein refers to an "unexamined published Japanese patent application"). Furthermore, it may correspond to the moiety which contains an aryl group which has been substituted with electron withdrawing groups and an atom (a sulfur atom, carbon atom or nitrogen atom) which links this to a photographically useful reagent in a compound which releases a photographically useful reagent with the cleavage of a single bond, following reduction, as disclosed in Japanese Patent Application (OPI) No. 142530/81 and in U.S. Pat. Nos. 4,343,893 and 4,619,884. Furthermore, it may correspond to the moiety which contains a nitro group and a carbon atom which links this to a photographically useful reagent in a nitro compound which releases a photographically useful reagent after receiving an electron as disclosed in U.S. Pat. No. 4,450,223, or it may correspond to the moiety which includes the geminal dinitro moiety and a carbon atom which bonds this to a photographically useful reagent in a dinitro compound in which a photographically useful reagent is β-eliminated after an electron has been accepted, as disclosed in U.S. Pat. No. 4,609,610. However, the PWR group in the compound represented by general formula (I) is preferably a group represented by general formula (II)

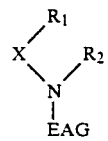 (II)

wherein

X represents an oxygen atom, a sulfur atom or a group —N(R$_3$)—; EAG represents an aromatic group capable of accepting at least one electron from a reducing substance; R$_1$, R$_2$ and R$_3$, which may be the same or different, each represents a substituted or unsubstituted alkyl group, a substituted or unsubstituted aralkyl group, a substituted or unsubstituted alkenyl group, a substituted or unsubstituted alkynyl group, a substituted or unsubstituted aryl group, a substituted or unsubstituted heterocyclic group, a substituted or unsubstituted acyl group, a substituted or unsubstituted sulfonyl group, a substituted or unsubstituted carbamoyl group, or a substituted or unsubstituted sulfamoyl group; provided that any of R$_1$, R$_2$, R$_3$ and EAG may be linked to form a 3-membered to 8-membered ring, at least one of R$_1$, R$_2$, R$_3$ and EAG is bonded to —[(Time)$_t$—(CG)$_n$]$_p$, at least one of R$_1$, R$_2$, R$_3$ and EAG is bonded to —(CG)$_m$, and R$_1$, R$_2$ and R$_3$ may each represent a single bond to —[(Time)$_t$—(CG)$_n$]$_p$ or —(CG)$_m$.

EAG will be described later;

R$_1$, R$_2$ and R$_3$ represent simple bonds or groups other than hydrogen atoms. In the latter case, preferred groups include, for example, alkyl groups, aralkyl groups (these may be substituted or unsubstituted alkyl groups or aralkyl groups, including, for example, a methyl group, trifluoromethyl group, benzyl group, chloromethyl group, dimethylaminomethyl group, ethoxycarbonylmethyl group, aminomethyl group, acetylaminomethyl group, ethyl group, 2-(4-dodecanoylaminophenyl)ethyl group, carboxyethyl group, allyl group, 3,3,3-trichloropropyl group, n-propyl group, isopropyl group, n-butyl group, isobutyl group, sec-butyl group, t-butyl group, n-pentyl group, sec-pentyl group, t-pentyl group, cyclopentyl group, n-hexyl group, sec-hexyl group, t-hexyl group, cyclohexyl group, n-octyl group, sec-octyl group, t-octyl group, n-decyl group, n-undecyl group, n-dodecyl group, n-tetradecyl group, n-pentadecyl group, n-hexadecyl group, sec-hexadecyl group, t-hexadecyl group, n-octadecyl group, t-octadecyl group, etc.), alkenyl groups (these may be substituted or unsubstituted alkenyl groups, including, for example, a vinyl group, 2-chlorovinyl group, 1-methylvinyl group, 2-cyanovinyl group, cyclohexen-1-yl group), alkynyl groups (these may be substituted or unsubstituted alkynyl groups, including, for example, an ethynyl group, 1-propynyl group, 2-ethoxycarbonylethynyl group), aryl groups (these may be substituted or unsubstituted aryl groups, including, for example, a phenyl group, naphthyl group, 30hydroxyphenyl group, 3-chlorophenyl group, 4-acetylaminophenyl group, 4-hexadecanesulfonylaminophenyl group, 2-methanesulfonyl-4-nitrophenyl group, 3-nitrophenyl group, 4-methoxyphenyl group, 4-acetylaminophenyl group, 4-methanesulfonylphenyl group, 2,4-dimethylphenyl group, 4-tetradecyloxyphenyl group), heterocyclic groups (these may be substituted or unsubstituted heterocyclic groups, including, for example, a 1-imidazolyl group, 2-furyl group, 2-pyridyl group, 5-nitro-2-pyridyl group, 3-pyridyl group, 3,5-dicyano-2-pyridyl group, 5-tetrazolyl group, 5-phenyl-1-tetrazolyl group, 2benzothiazolyl group, 2-benzimidazolyl group, 2-benzoxazolyl group, 2-oxazolin-2-yl group, morpholino group, etc.), acyl groups (these may be substituted or unsubstituted acyl groups, including, for example, an acetyl group, propionyl group, butyrolyl group, isobutyroyl group, 2,2-dimethylpropionyl group, benzoyl group, 3,5-dichlorobenzyl group, 3-acetylamino-4-methoxybenzoyl group, 4-methylbenzoyl group, 4-methoxy-3-sulfobenzoyl group, etc.), sulfonyl groups (these may be substituted or unsubstituted sulfonyl groups, including, for example, a methaensulfonyl group, ethanesulfonyl group, chloromethanesulfonyl group, propanesulfonyl group, butanesulfonyl group, n-octanesulfonyl group, n-dodecanesulfonyl group, n-hexadecanesulfonyl group, benzenesulfonyl group, 4-toluenesulfonyl group, 4-n-dodecyloxybenzenesulfonyl group, etc.), carbamoyl groups (these may be substituted or unsubstituted carbamoyl groups, including, for example, a carbamoyl group, methylcarbamoyl group, dimethylcarbamoyl group, bis-(2-methoxyethyl)carbamoyl group, diethylcarbamoyl group, cyclohexylcarbamoyl group, di-n-octylcarbamoyl group, 3-dodecyloxypropylcarbamoyl group, hexadecylcarbamoyl group, 3-(2,4-di-t-pentylphenoxy)propylcarbamoyl group, 3-octanesulfonylaminophenylcarbamoyl group, di-n-octadecylcarbamoyl group, etc.), sulfamoyl groups (these may be substituted or unsubstituted sulfamoyl groups, including, for example, a sulfamoyl group, methylsulfamoyl group, dimethylsulfamoyl group, diethylsulfamoyl group, bis-(2-methoxyethyl)sulfamoyl group, di-n-butylsulfamoyl group, methyl-n-octylsulfamoyl group, n-hexadecylmethylsulfamoyl group, 3-ethoxypropylmethylsulfamoyl group, N-phenyl-N-methylsulfamoyl group, 4-decyloxyphenylsulfamoyl group, methyloctadecylsulfamoyl group, etc.). Moreover, any of $R_1$, $R_2$, $R_3$ and EAG may be linked to form a 3- to 8-membered ring.

When, in general formula (I), $(CG)_m$ and $[(Time)_r-(CG)_n]_p$ are bonded to a PWR moiety represented by general formula (II), they are bonded to at least one of $R_1$, $R_2$, $R_3$ and EAG in formula (II).

With respect to the function and synthesis, the PWR unit represented by general formula (II) is preferably a unit represented by general formula (III):

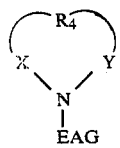

(III)

wherein Y represents a divalent linking group, preferably a

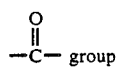 group or an $-SO_2-$ group; $R_4$ represents an atomic group necessary for forming a 5- to 8-membered simple or condensed heterocyclic ring; and X and EAG each is defined as in formula (II).

Examples of preferred heterocyclic rings formed from $R_4$, X, N and Y are shown below, and EAG is also included.

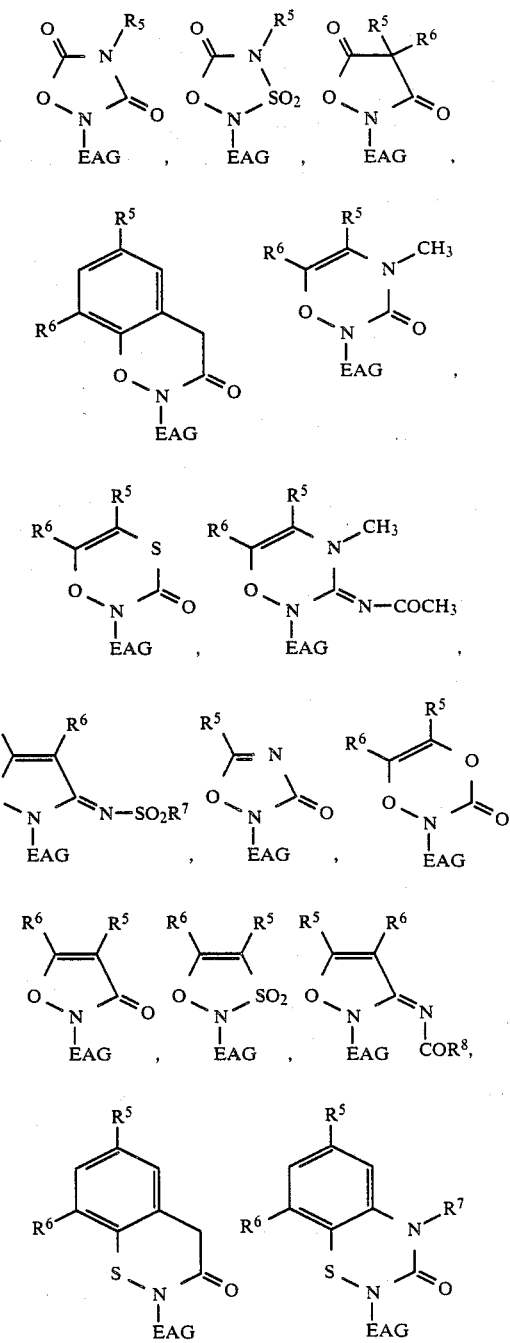

-continued

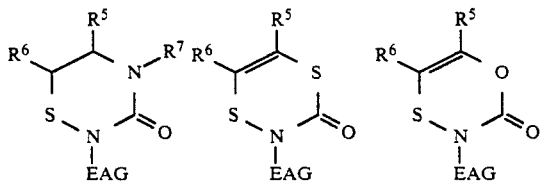

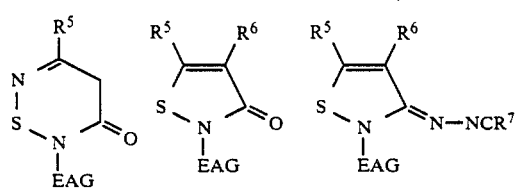

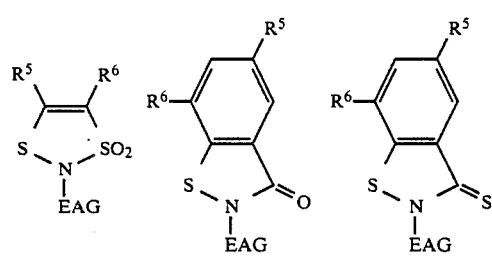

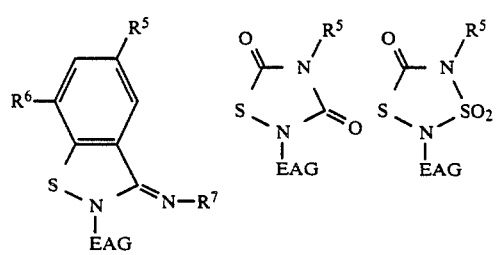

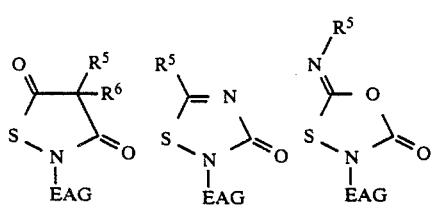

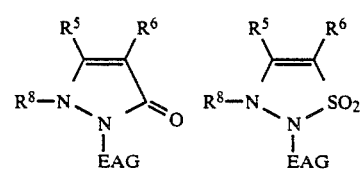

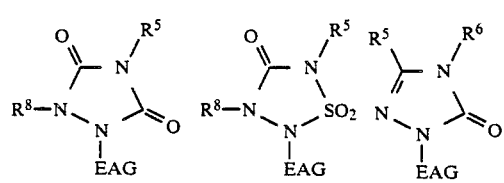

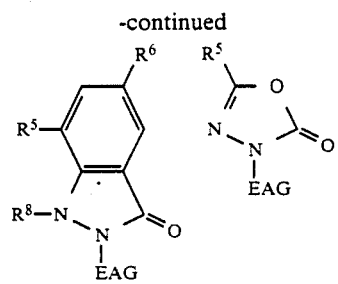

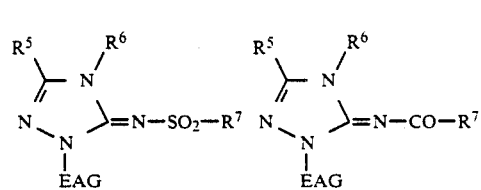

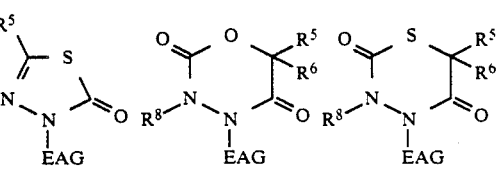

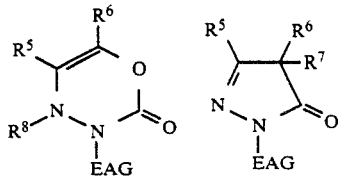

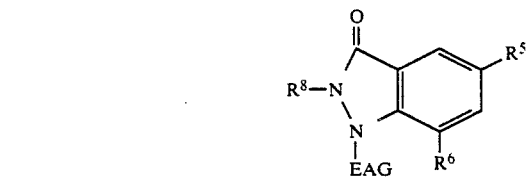

wherein $R^5$, $R^6$ and $R^7$, which may be the same or different, each represents a hydrogen atom, alkyl group, aryl group or heterocyclic group, and $R^8$ represents an acyl group or a sulfonyl group, etc.

Where $(CG)_m$ and $[(Time)_t-(CG)_n]_p$ in general formula (I) are bonded to a PWR unit represented by the general formula (III), they are bonded to at least one of $R_3$, $R_4$ and EAG in formula (III).

The EAG is now described in greater detail.

Thus EAG represents an aromatic group capable of accepting electrons from a reducing substance and it is bonded to a nitrogen atom. Groups represented by general formula (A) below are preferred for the EAG.

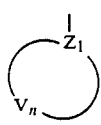

(A)

wherein $Z_1$ represents a

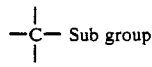

or an

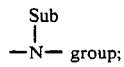

V represents an atomic group necessary for forming a 3- to 8-membered aromatic ring containing members selected from

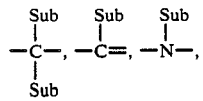

—N═, —O—, —S— and —SO$_2$— wherein sub represents a hydrogen atom or a substituent group, as indicated below, plural Sub groups may be the same or different, and at least two Sub groups may be linked to form a 3- to 8-membered saturated or unsaturated carbocyclic or heterocyclic ring; provided that the total sum of the Hammett substituent constants ($\sigma_p$) of the substituent is at least +0.50, preferably at least +0.70 and most preferably at least +0.85.

EAG represents a group which accepts electrons from a reducing substance and it is bonded to the nitrogen atom. The EAG is preferably a heterocyclic group or an aryl group, each substituted with at least one electron withdrawing group. The substituent groups bonded to the aryl group or the heterocyclic group of EAG can be used to adjust the properties of the compound as a whole. Examples of properties of the compound as a whole which can be adjusted include, as well as adjustment of the ease with which an electron can be accepted, water solubility, oil solubility, diffusion properties, sublimation properties, melting point, dispersibility, in gelatins, reactivity with respect to nucleophilic groups and reactivity with respect to electrophilic groups, and examples of suitable substituent groups include linking groups for bonding the (CG)$_m$ and [(Time)$_t$—(CG$_n$]$_p$ units in general formula (I) or the (CG)$_m$ and [(Time)$_t$—(CG$_n$]$_p$ units in general formula (I) themselves.

Specific examples of EAG are indicated below, but the present invention is not to be construed as being limited thereto.

Examples of aryl groups substituted with at least one electron withdrawing group include, for example, a 4-nitrophenyl group, 2-nitrophenyl group, 2-nitro-4-N-methyl-N-n-butylsulfamoylphenyl group, 2-nitro-4-N-methyl-N-n-octylsulfamoylphenyl group, 2-nitro-4-N-methyl-N-n-dodecylsulfamoylphenyl group, 2-nitro-4-N-methyl-N-n-hexadecylsulfamoylphenyl group, 2-nitro-4-N-methyl-N-n-octadecylsulfamoylphenyl group, 2-nitro-4-N-methyl-N-(3-carboxypropyl)sulfamoylphenyl group, 2-nitro-4-N-ethyl-N-(2-sulfoethyl)sulfamoylphenyl group, 2-nitro-4-N-n-hexadecyl-N-(3-sulfopropyl)sulfamoylphenyl group, 2-nitro-4-N-(2-cyanoethyl)-N-((2-hydroxyethoxy)ethyl)sulfamoylphenyl group, 2-nitro-4-diethylsulfamoylphenyl group, 2-nitro-4-di-n-butylsulfamoylphenyl group, 2-nitro-4-di-n-octylsulfamoylphenyl group, 2-nitro-4-di-n-octadecylsulfamoylphenyl group, 2-nitro-4-methylsulfamoylphenyl group, 2-nitro-4-n-hexadecylsulfamoylphenyl group, 2-nitro-4-N-methyl-N-(4-dodecylsulfonylphenyl)sulfamoylphenyl group, 2-nitro-4-(3-methylsulfamoylphenyl)sulfamoylphenyl group, 4-nitro-2-N-methyl-N-n-butylsulfamoylphenyl group, 4-nitro-2-N-methyl-N-n-octylsulfamoylphenyl group, 4-nitro-s-N-methyl-N-n-dodecylsulfamoylphenyl group, 4-nitro-2-N-methyl-N-n-hexadecylsulfamoylphenyl group, 4-nitro-2-N-methyl-N-n-octadecylsulfamoylphenyl group, 4-nitro-2-N-methyl-N-(3-carboxypropyl)sulfamoylphenyl group, 4-nitro-2-N-ethyl-N-(2-sulfoethyl)sulfamoylphenyl group, 4-nitro-2-N-n-hexadecyl-N-(3-sulfopropyl)sulfamoylphenyl group, 4-nitro-2-N-(2-cyanoethyl)-N-((2-hydroxyethoxy)ethyl)sulfamoylphenyl group, 4-nitro-2-diethylsulfamoylphenyl group, 4-nitro-2-di-n-butylsulfamoylphenyl group, 4-nitro-2-di-n-octylsulfamoylphenyl group, 4-nitro-2-di-n-octadecylsulfamoylphenyl group, 4-nitro-2-methylsulfamoylphenyl group, 4-nitro-2-n-hexadecylsulfamoylphenyl group, 4-nitro-2-N-methyl-N-(4-dodecylsulfonylphenyl)sulfamoylphenyl group, 4-nitro-2-(3-methylsulfamoylphenyl)sulfamoylphenyl group, 4-nitro-2-chlorophenyl group, 2-nitro-4-chlorophenyl group, 2-nitro-4-N-methyl-N-n-butylcarbamoylphenyl group, 2-nitro-4-N-methyl-N-n-octylcarbamoylphenyl group, 2-nitro-4-N-methyl-N-n-dodecylcarbamoylphenyl group, 2-nitro-4-N-methyl-N-n-hexadecylcarbamoylphenyl group, 2-nitro-4-N-methyl-N-n-octadecylcarbamoylphenyl group, 2-nitro-4-N-methyl-n-(3-carboxypropyl)carbamoylphenyl group, 2-nitro-4-N-ethyl-N-(2-sulfoethyl)carbamoylphenyl group, 2-nitro-4-N-n-hexadecyl-N-(3-sulfopropyl)carbamoylphenyl group, 2-nitro-4-N-(2-cyanoethyl)-N-((2-hydroxyethoxy)ethyl)carbamoylphenyl group, 2-nitro-4-diethylcarbamoylphenyl group, 2-nitro-4-di-n-butylcarbamoylphenyl group, 2-nitro-4-di-n-octylcarbamoylphenyl group, 2-nitro-4-di-n-octadecylcarbamoylphenyl group, 2-nitro-4-methylcarbamoylphenyl group, 2-nitro-4-n-hexadecylcarbamoylphenyl group, 2-nitro-4-N-methyl-N-(4-dodecylsulfonylphenyl)carbamoylphenyl group, 2-nitro-4-(3-methylsulfamoylphenyl)carbamoylphenyl group, 4-nitro-2-N-methyl-N-n-butylcarbamoylphenyl group, 4-nitro-2-N-methyl-n-n-octylcarbamoylphenyl group, 4-nitro-2-N-methyl-N-n-dodecylcarbamoylphenyl group, 4-nitro-2-N-methyl-N-n-hexadecylcarbamoylphenyl group, 4-nitro-2-N-methyl-N-n-octadecylcarbamoylphenyl group, 4-nitro-2-N-methyl0-N-(3-carboxypropyl)carbamoylphenyl group, 4-nitro-2-N-ethyl-N-(2-sulfoethyl)carbamoylphenyl group, 4-nitro-2-N-n-hexadecyl-N-(3-sulfopropyl)carbamoylphenyl group, 4-nitro-2-N-(2-cyanoethyl)-N-((2-hydroxyethoxy)ethyl)carbamoylphenyl group, 4-nitro-2-diethylcarbamoylphenyl group, 4-nitro-2-di-n-butylcarbamoylphenyl group, 4-nitro-2-di-n-octylcarbamoylphenyl group, 4-nitro-2-di-n-octadecylcarbamoylphenyl group, 4-nitro-2-methylcarbamoylphenyl group, 4-nitro-2-n-hexadecylcarbamoylphenyl group, 4-nitro-2-N-methyl-N-(4-dodecylsulfonylphenyl)carbamoylphenyl group, 4-nitro-2-(3-methylsulfamoylphenyl)carbamoylphenyl group, 2,4-dimethanesulfonylphenyl group, 2-methanesulfonyl-4-benzenesulfonylphenyl group, 2-n-octanesulfonyl-4-methanesulfonylphenyl, group, 2-n-tetradecanesulfonyl-4-methanesulfonylphenyl group, 2-n-hexadecanesulfonyl-4-methanesulfonylphenyl group, 2,4-di-n-dodecanesulfonylphenyl group, 2,4-didodecanesulfonyl-5-trifluoromethylphenyl group, 2-n-decanesulfonyl-4-cyano-5-trifluoromethylphenyl group, 2-cyano-4-methanesulfonylphenyl group, 2,4,6-tricyanophenyl group, 2,4-dicyanophenyl group, 2-nitro-4-methanesulfonylphenyl group, 2-nitro-4-n-dodecanesulfonylphenyl group, 2-nitro-4-(2-sulfoethylsulfonyl)phenyl group, 2-nitro-4-carboxymethylsulfonylphenyl group, 2-nitro-4-carboxyphenyl group, 2-nitro-4-ethoxycarbonyl-5-n-butoxyphenyl group, 2-nitro-4-ethoxycarbonyl-5-n-hexadecyloxyphenyl group, 2-nitro-4-diethylcarbamoyl-5-n-hexadecyloxyphenyl group, 2-nitro-4-cyano-B 5-n-dodecylphenyl group, 2,4-dinitrophenyl group, 2-nitro-4-n-decylthiophenyl group, 3,5-dinitrophenyl group, 2-nitro-3,5-dimethyl-4-n-hexadecanesulfonylphenyl group, 4-methanesulfonyl-2-benzenesulfonylphenyl group, 4-n-octanesulfonyl-2-methanesulfonylphenyl group, 4-n-tetradecanesulfonyl-2-methanesulfonylphenyl group, 4-n-hexadecanesulfonyl-2methanesulfonylphenyl group, 2,5-didodecanesulfonyl-4-trifluoromethylphenyl group, 4-n-decanesulfonyl-2-cyano-5-trifluoromethylphenyl group, 4-cyano-2-methanesulfonylphenyl group, 4-nitro-2-methanesulfonylphenyl group, 4-nitro-2-n-dodecanesulfonylphenyl group, 4-nitro-2-(2-sulfoethylsulfonyl)phenyl group, 4-nitro-2-carboxymethylsulfonylphenyl group, 4-nitro-2-carboxyphenyl group, 4-nitro-2-ethoxycarbonyl-5-n-butoxyphenyl group, 4-nitro-2-ethoxycarbonyl-5-n-hexadecyloxyphenyl group, 4-nitro-2-diethylcarbamoyl-5-n-hexadecyloxyphenyl group, 4-nitro-2-cyano-5-n-dodecylphenyl group, 4-nitro-2-n-decylthiophenyl group, 4-nitro-3,5-dimethyl-2-n-hexadecanesulfonylphenyl group, 4-nitro-naphthyl group, 2,4-dinitronaphthyl group, 4-nitro-2-n-octadecylcarbamoylnaphthyl group, 4-nitro-2-dioctylcarbamoyl-5-(3-sulfobenzenesulfonylamino)naphthyl group, 2,3,4,5,6-pentafluorophenyl group, 2-nitro-4-benzoylphenyl group, 2,4-diacetylphenyl group, 2-nitro-4-trifluoromethylphenyl group, 4-nitro-2-trifluoromethylphenyl group, 4-nitro-3-trifluoromethylphenyl group, 2,4,5-tricyanophenyl group, 3,4-dicyanophenyl group, 2-chloro-4,5-dicyanophenyl group, 2-bromo-4,5-dicyanophenyl group, 4-methanesulfonylphenyl group, 4-n-hexadecanesulfonylphenyl group, 2-decanesulfonyl-5-trifluoromethylphenyl group, 2-nitro-5-methylphenyl group, 2-nitro-5-n-octadecyloxyphenyl group, 2-nitro-4-N-(vinylsulfonylethyl)-n-methylsulfamoylphenyl group, 2-methyl-6-nitrobenzoxazol-5-yl group, etc.; and examples of heterocyclic groups include a 2-pyridyl group, 3-pyridyl group, 4-pyridyl group, 5-nitro-2-pyridyl group, 5-nitro-N-hexadecylcarbamoyl-2-pyridyl group, 3,5-dicyano-2-pyridyl group, 5-dodecanesulfonyl-2-pyridyl group, 5-cyano-2-pyrazyl group, 4-nitro-thiophen-2-yl group, 5-nitro-1,2-dimethylimidazol-4-yl group, 3,5-diacetyl-2-pyridyl group, 1-dodecyl-5-carbamoylpyridinium-2-yl group, 5-nitro-2-furyl group, 5-nitrobenzthiaol-2-yl group, etc.

The —(Time)$_t$— unit is described in greater detail below.

Time represents a group capable of releasing CG subsequent to the cleavage of a nitrogen-oxygen, nitrogen-nitrogen or a nitrogen-sulfur bond in PWR.

Various groups which can be represented by Time are known, for example, those disclosed on pages 5 and 6 of Japanese Patent Application (OPI) No. 14724/86, those disclosed on pages 8 to 14 of Japanese Patent Application (OPI) No. 236549/86 and those disclosed on pages 17 to 36 of Japanese Patent Application No. 244873/85.

Preferred examples of the Time group are shown below. Here the asterisk (*) indicates the position of bonding to PWR in general formula (I) and the double asterisk (*)(*) indicates the position at which CG is bonded.

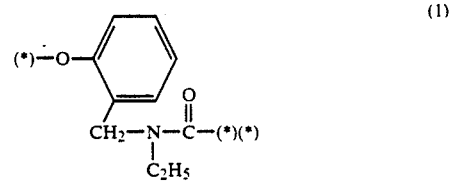

(1)

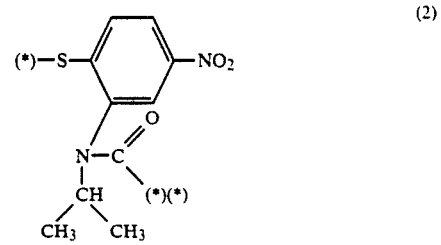

(2)

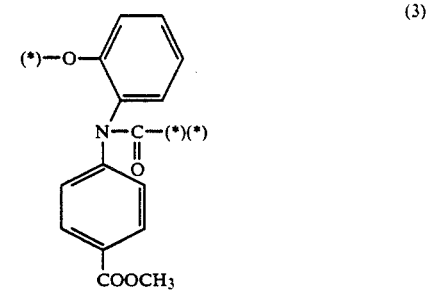

(3)

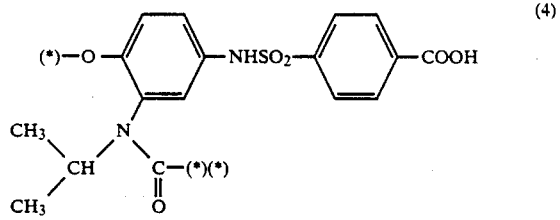

(4)

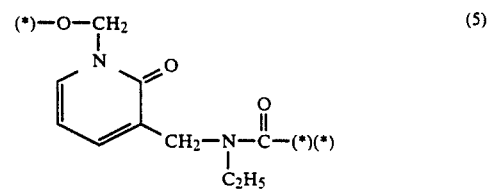

(5)

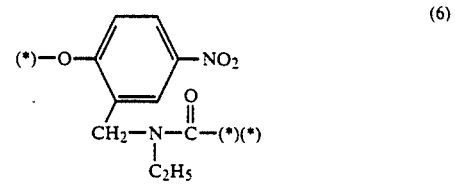

(6)

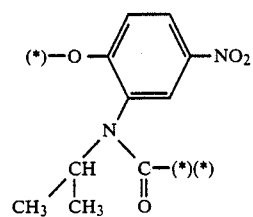
(7)
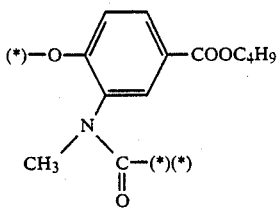
(8)
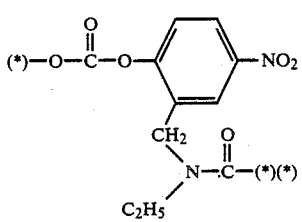
(9)
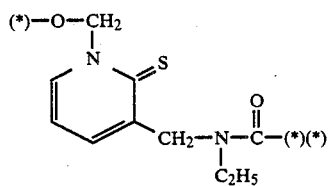
(10)
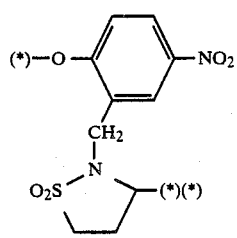
(11)
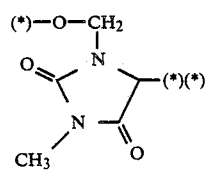
(12)
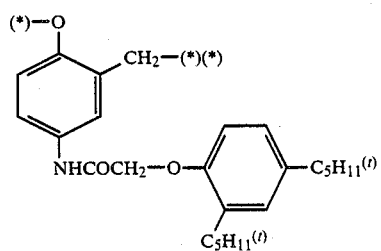
(13)
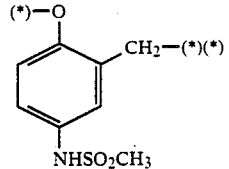
(14)
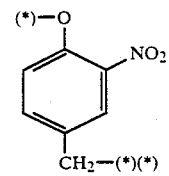
(15)
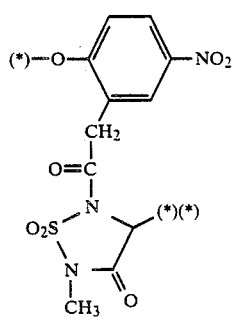
(16)
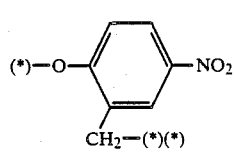
(17)
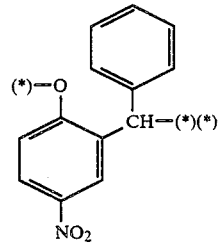
(18)
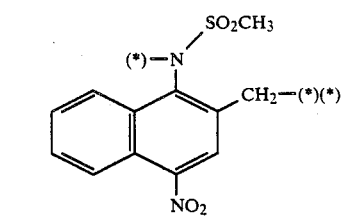
(19)
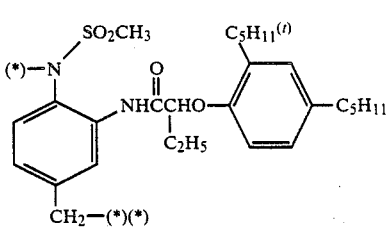
(20)

-continued

(21) — 4-nitro-3-... (structure with O(*), NO2, phenyl-CH(*)(*), C12H25)

(22) — pyrazole structure with O(*), CH2-(*)(*), CH3, N-phenyl

(23) — pyrazole with O(*), CH2-(*)(*), CH3-N, CON(C8H17)2

(24) — pyrazole with O(*), CH2-(*)(*), CN, N-(4-nitrophenyl)

(25) — (*)—O(CH2)3N(cyclohexyl)—C(=O)—(*)(*)

(26) — (*)—O—C(=O)—N(CH3)(CH2)2N(CH3)—C(=O)—(*)(*)

(27) — pyridine with O(*), CH2-(*)(*)

(28) — pyrazole with O(*), CH2-(*)(*), N-(2,4,6-trichlorophenyl), NH-C(=O)-CH2-O-phenyl(2,4-di-tert-C5H11)

-continued

(29) — pyrazole with O(*), CH2-(*)(*), CH3-N, COOH

(30) — (*)—O(CH2)2—N(CH(CH3)2)—C(=O)—(*)(*)

(31) — naphthalene with O(*), N(CHO)—C(=O)—(*)(*)

(32) — (*)—O—C(=O)—O(CH2)2—N(CH3)—C(=O)—(*)(*)

(33) — (*)—O—CH2—(*)(*)

(34) — (*)—S—CH(COOC2H5)—(*)(*)

(35) — (*)—O—CH(C(=O)phenyl)—(*)(*)

(36) — (*)—O—CH2—N(SO2NH-phenyl)—CH2—(*)(*)

(37) — (*)—O—CH2—N(4-methoxyphenyl)—CH2—(*)(*)

(38) — (*)—O—C(=O)—N(C2H5)-(4-nitro-2-CH2-(*)(*)-phenyl)

(39) — (*)—O—C(=O)—N(C2H5)-(4-(C11H23)CH-(*)(*)-2-nitrophenyl)

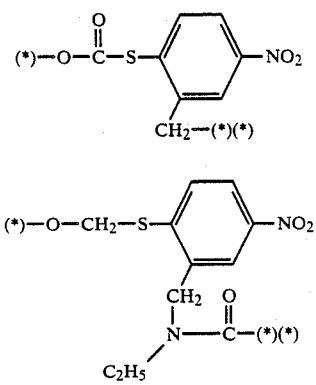
(40)
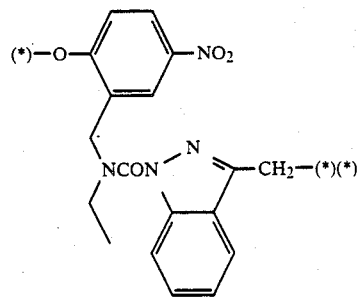
(42)
Specific examples of compounds represented by general formula (I) include the following, but the present invention is not to be construed as being limited thereto:
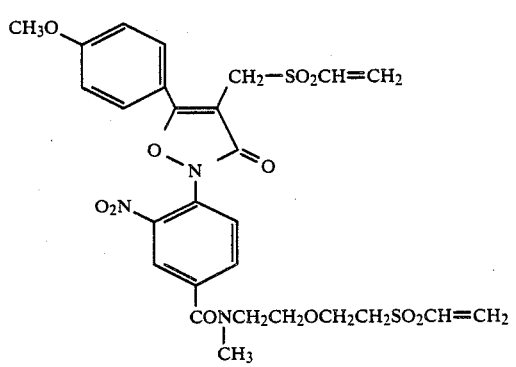
(1)
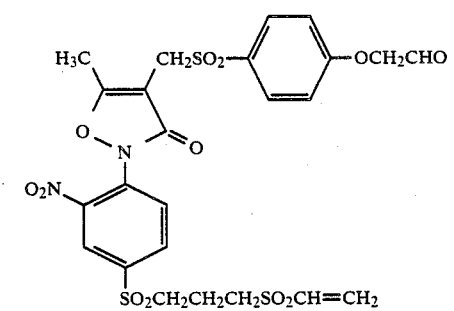
(2)
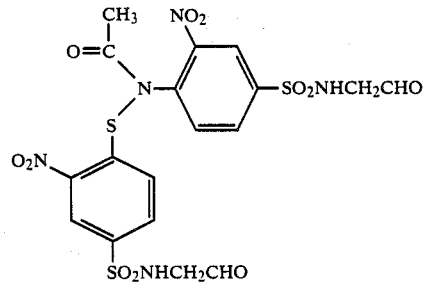
(3)

-continued
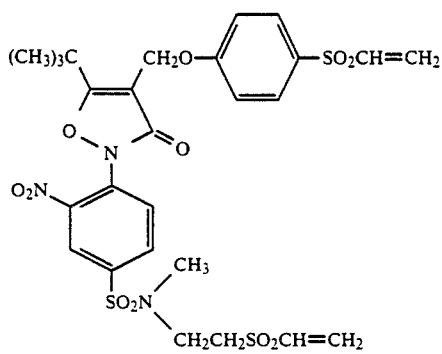
(4)
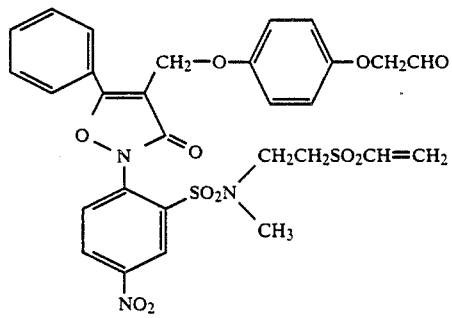
(5)
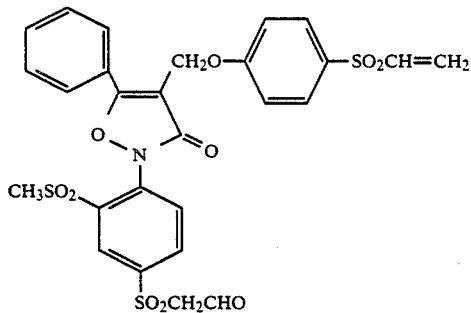
(6)
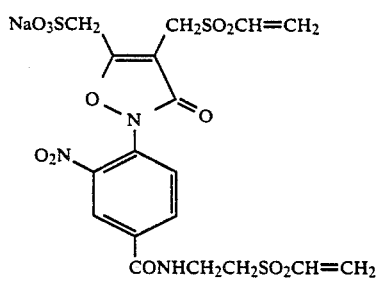
(7)
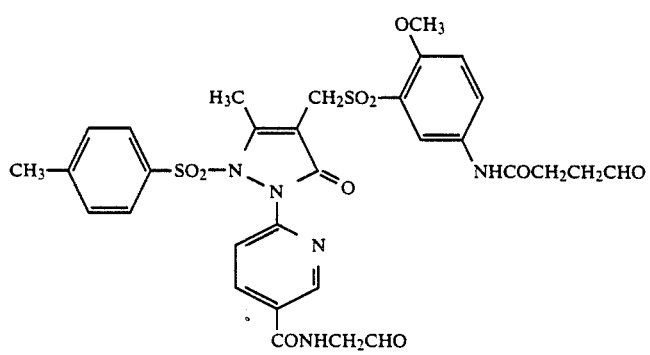
(8)

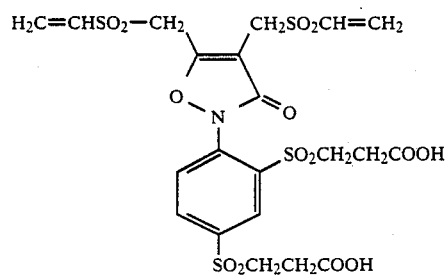 (9)
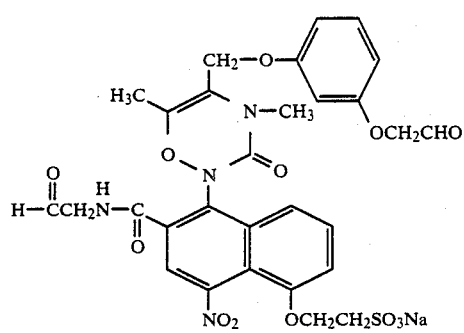 (10)
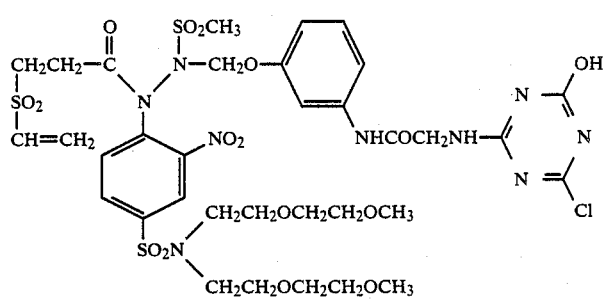 (11)
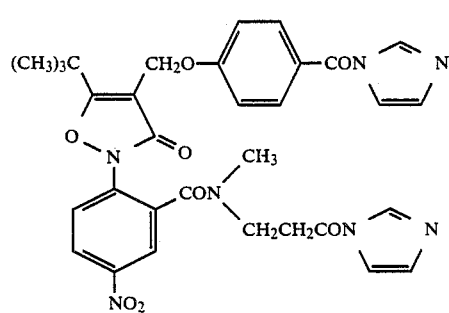 (12)
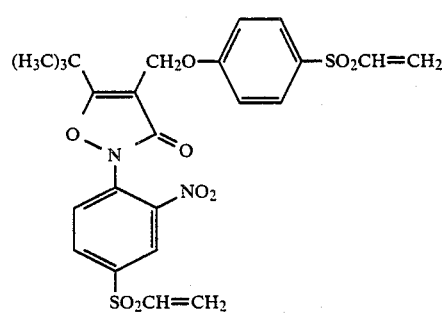 (13)

-continued
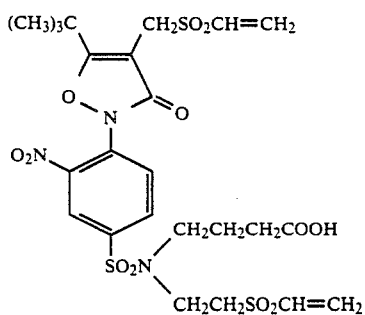 (14)
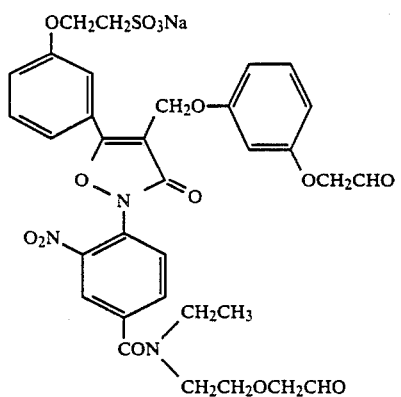 (15)
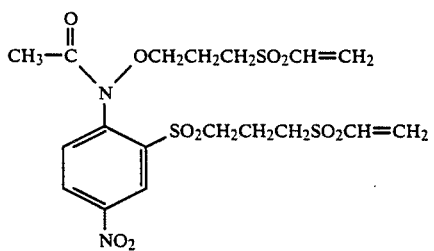 (16)
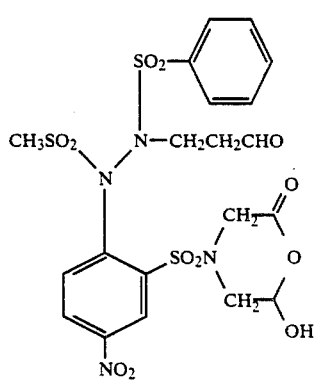 (17)

-continued
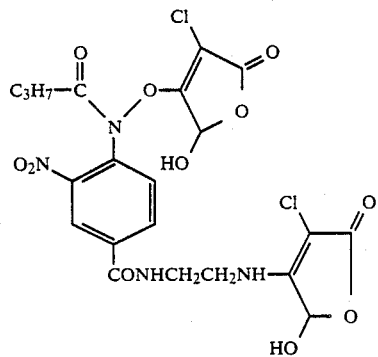 (18)
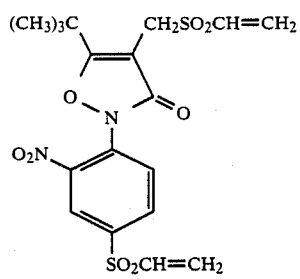 (19)
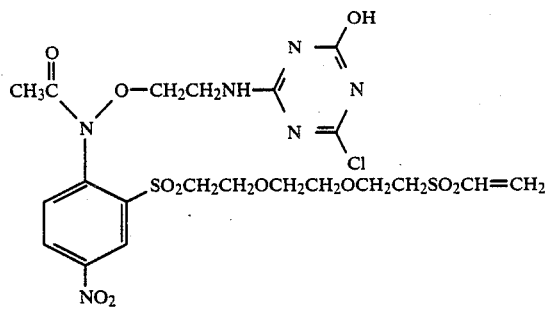 (20)
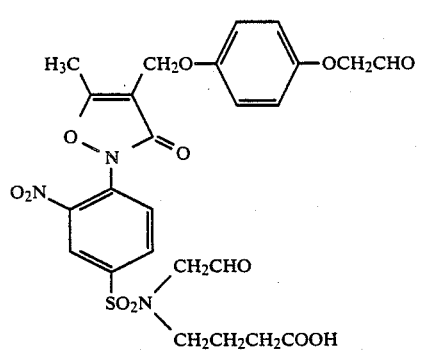 (21)
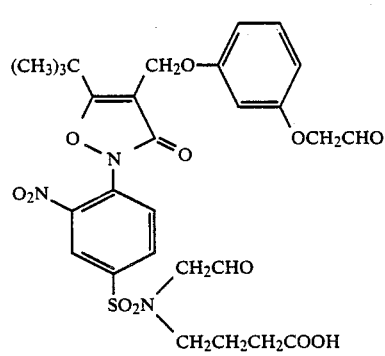 (22)

Methods for the synthesis of the compounds used in the invention are described in detail below.

The synthesis of the part represented by PWR in the compounds of general formula (I) can be achieved by the methods shown in publications in which the PWR units have been described in detail (U.S. Pat. Nos. 4,139,389, 4,139,379 and 4,564,577, Japanese Patent Application (OPI) Nos. 185333/84 and 84453/82, U.S. Pat. No. 4,232,107, Japanese Patent Application (OPI) No. 101649/84, Research Disclosure (1984), IV, No. 24025, Japanese Patent Application (OPI) No. 88257/86, DT-OS 3,008,588, Japanese Patent Application (OPI) No. 142530/81 and U.S. Pat. Nos. 4,343,893, 4,619,884, 4,450,223 and 4,609,610). Methods for the synthesis of the part corresponding to PWR of the compounds represented by general formula (II) are described in detail hereinafter. The aforementioned patents also disclose methods for the linking of the [(Time)$_t$—(CG)$_n$] unit.

Methods for the synthesis of compounds represented by general formula (II) have been described in Japanese Patent Application (OPI) Nos. 215270/87, and 244048/87, and Japanesen Patent Application Nos. 34954/87 and 34953/87.

SYNTHESIS EXAMPLE 1

Synthesis of Compound 19

Step 1: Synthesis of 5-t-butyl-3-hydroxyiso-oxazole

This compound can be prepared easily using the methods described in the following sources: Mitsui Research Laboratories Annual Reports, Vol. 22, page 215 (1970); Japanese Patent Publication No. 9675/77; *Bulletin de la Societe Chimique de France*, page 1978; Japanese Patent Application (OPI) Nos. 206668/82 and 206667/82; *Tetrahedron*, Vol. 20, page 2835 (1964); Japanese Patent Application (OPI) Nos. 194867/83, 70878/82, Japanese Patent Publication No. 48953/74 and Japanese Patent Application (OPI) No. 190977/84; *Journal of Organic Chemistry*, Vol. 48, page 4307 (1983); *Chemical and Pharmaceutical Bulletin*, Vol. 14, page 277; *Heterocycles*, Vol. 12, No. 10, page 1297; *Canadian Journal of Chemistry*, Vol. 62, page 1940; and WO8401774.

In one suitable illustrative method, 583.7 g of hydroxylamine hydrochloride was dissolved in 2 liters of 4N aqueous sodium hydroxide solution and 2 liters of ethanol was added with ice cooling, after which a mixture of 4N aqueous sodium hydroxide solution and ethanol (1:1) was added to adjust pH of the solution to 10.0. Next 1380 g of ethyl pivaloylacetate and a mixture of 4N aqueous sodium hydroxide solution and ethanol (1:1) were added dropwise to this solution to adjust the pH of the reaction mixture to 10.0±0.2, while maintaining a reaction mixture temperature of 0° to 5° C.

Once the dropwise addition had been completed, the reaction mixture was stirred for a period of 2 hours at room temperature, after which it was poured into 6 kg of aqueous concentrated hydrochloric acid at 0° C. and left to stand for a period of 12 hours. The crystals which precipitated out were recovered by filtration and dried after being washed thoroughly with water.

Recovery 770 g, yield 78.2%, Melting Point 99°–101° C.

Step 2: Synthesis of 2-(4-Chloro-3-nitrobenzenesulfonyl)ethanol 40 g of 4-Chloro-3-nitrobenzenesulfinic acid, 27.8 g of potassium carbonate, 24.8 g of 2-bromoethanol and 200 ml of dimethylformamide were mixed together and reacted at 50° C. for a period of 8 hours. The reaction mixture was then poured into of water and extracted with ethyl acetate. The organic layer was recovered and the solvent was removed by distillation under reduced pressure. The oily residue was refined using silica gel short-column chromatography to obtain an oily product.

Recovery 31.1 g, Yield 64.9%.

Step 3: Synthesis of 5-t-Butyl-2-(4-(2-hydroxyethylsulfonyl)-2-nitrophenyl)-4-iso-oxazolin-3-one 30 g of 2-(4-chloro-3-nitrobenzenesulfonyl)ethanol, 19.1 g ot 5-t-butyl-3-hydroxyiso-oxazole, 28 g of sodium bicarbonate and 200 ml of dimethylsulfoxide were mixed together and reacted at 80° C. for a period of 8 hours. After cooling, the reaction mixture was poured into of water and the mixture was extracted with ethyl acetate. The organic layer was recovered and, after removing the solvent by distillation under reduced pressure, the main product was isolated using silica gel column chromatography as an oily product.

Recovery 25.9 g, Yield 61.9%.

Step 4: Synthesis of 5-t-Butyl-4-chloromethyl-2-(4-(2-hydroxyethylsulfonyl)-2-nitrophenyl)-4-isooxazolin-3-one 20 g of 5-t-Butyl-2-(4-(2-hydroxyethylsulfonyl)-2-nitrophenyl)-4-isooxazolin-3-one, 15 g of zinc chloride, 15 g of paraformaldehyde and 100 ml of acetic acid were mixed together, 1 ml of concentrated sulfuric acid was added, and the mixture was reacted at 95° C. for a period of 8 hours while blowing 60 l/hr of hydrogen chloride gas into the reaction mixture. After cooling, 300 ml of water was added and the mixture was extracted with ethyl acetate. The organic acid layer was washed three times with aqueous sodium bicarbonate solution and then the target compound was obtained by distilling the solvent off from the organic layer to obtain an oily product.

Recovery 20.1 g, Yield 88.9%.

Step 5: Synthesis of 5-t-Butyl-4-(2-hydroxyethylthiomethyl)-2-(4-(2-hydroxyethylsulfonyl)-2-nitrophenyl)-4-iso-oxazolin-3-one 15 g of 5-t-Butyl-4-chloromethyl-2-(4-(2-hydroxyethylsulfonyl)-2-nitrophenyl)-4-iso-oxazolin-3-one was dissolved in 150 ml of tetrahydrofuran, 2.8 g of 2-hydroxyethanethiol and 4 g of triethylamine were added and the mixture was reacted at room temperature for a period of 5 hours. After reaction, the solvent was removed by distillation, ethyl acetate and water (150 ml:100 ml) were added and the mixture was partitioned. The organic layer was recovered, the solvent was removed by distillation and the residue obtained was used without further refinement in step 6.

Step 6: Synthesis of 5-t-Butyl-4-(2-hydroxyethylsulfonylmethyl)-2-(4-(2-hydroxyethylsulfonyl)-2-nitrophenyl)-4-iso-oxazolin-3-one Acetic acid (100 ml) was added to the 5-t-butyl-4-(2-hydroxyethylthiomethyl)-2-(4-(2-hydroxyethylsulfonyl)-2-nitrophenyl)-4-iso-oxazolin-3-one prepared in step 5 and the mixture was heated to 70° C. on a steam bath. Next, 9.4 g of 35% hydrogen peroxide was added dropwise while maintaining the temperature within the range from 80° to 85° C. After reaction, the reaction mixture was poured into water and extracted with ethyl acetate. The main product was obtained using flash silica gel column chromatography after removing the solvent from the extract as an oily product.

Recovery 10.8 g, Yield 61.2% (two operations)

Step 7: Synthesis of Compound 19

5 g of 5-t-Butyl-4-(2-hydroxyethylsulfonylmethyl)-2-(4-(2-hydroxyethylsulfonyl)-2-nitrophenyl)-4-isooxazolin-3-one was dissolved in 50 ml of ethyl acetate and 2.1 g of acetic anhydride was added. The mixture was cooled to 0° C. and 4 g of triethylamine was added slowly in a dropwise manner. The ethyl acetate was removed by distillation under reduced pressure after 1 hour and the residue was refined using flash silica gel column chromatography.

Recovery 2.8 g, Yield 60.1%. Melting point: 160°–163° C. (Decomp.)

The silver halide photographic materials of the invention have at least one gelatin layer which is crosslinked by means of a crosslinking agent of the aforementioned type. This gelatin layer may be a photosensitive layer or it may be some other structural layer (for example, a protective layer, intermediate layer, filter layer, antihalation layer, backing layer, etc.).

The aforementioned crosslinking agents can be used in any quantity in this invention, but in general they are used an amount of at least about 0.1 mmol/m$^2$ of the material and they are preferably used in amounts within the range from about 1 mmol/m$^2$ to 400 mmol/m$^2$ of the material. They can also be used together with the other film hardening agents mentioned later.

The gelatin used in the invention may be lime treated gelatin or acid treated gelatin, or alternatively it may be an enzyme treated gelatin as disclosed in *Bull. Soc. Sci. Phot. Japan*, No. 16, page 30 (1966), and hydrolyzed and enzyme degraded gelatins can also be used. Gelatin derivatives obtained by reacting gelatin with various compounds, such as acid halides, acid anhydrides, isocyanates, bromoacetic acid, alkanesultone, vinylsulfonamides, maleimido compounds, polyalkyleneoxides, epoxy compounds, etc. can be used as gelatin derivatives. Specific examples have been disclosed in U.S. Pat. Nos. 2,614,928, 3,132,945, 3,186,846 and 3,312,553, British Patents 861,414, 1,033,189 and 1,005,784, and in Japanese Patent Publication No. 26845/67, etc.

Gelatin graft polymers obtained by grafting gelatin with homopolymers or copolymers of vinyl based monomers such as acrylic acid, methacrylic acid, derivatives such as esters and amides of these acids, acrylonitrile, styrene, etc. can also be used as the aforementioned gelatin graft polymers. Moreover, graft polymers formed with polymers which are compatible to a certain extent with gelatin, such as polymers of acrylic acid, methacrylic acid, acrylamide, methacrylamide, hydroxyalkyl methacrylate, etc. are preferred. Examples of these have been disclosed in U.S. Pat. Nos. 2,763,625, 2,831,767 and 2,956,884, etc.

In gelatin layers which have been crosslinked with a crosslinking agent of this invention, the crosslinks are broken on the acceptance of an electron from a reducing substance. Hence the mechanical strength of the gelatin film is adequate prior to the attack by a reducing substance during processing, and the water washing properties are improved because the extent of the crosslinking is reduced during processing. It is possible in this invention to control the strength of the gelatin during processing so that it is able to stand up to the processing operation by using the aforementioned crosslinking agents conjointly with other crosslinking agents (i.e., crosslinking agents of which the crosslinks are not broken by reduction).

The reducing substances used for the reduction of the compounds can be inorganic compounds or organic compounds, and their oxidation potential is preferably lower than the standard oxidation-reduction potential of silver ion/silver, which is 0.80 V.

Examples of useful inorganic compounds include metals having an oxidation potential of 0.80 V or less, such as Mn, Ti, Si, Zn, Cr, Fe, Co, Mo, Sn, Pb, W, H$_2$, Sb, Cu and Hg; ions and complexes thereof having an oxidation potential of 0.80 V or less, such as Cr$^{2+}$, V$^{2+}$, Cu$^+$, Fe$^{2+}$, MnO$_4{}^{2-}$, I$^-$, Co(CN)$_5{}^{4-}$, Fe(CN)$_5{}^{4-}$, (FeEDTA)$^{2-}$; metal hydrides having an oxidation potential of 0.80 V or less, such as NaH, LiH, KH, NaBH$^4$, LiBH$_4$, LiAl(O-tC$_4$H$_9$)$_3$H, LiAl(OCH$_3$)$_3$H; sulfur or phosphorus compounds having an oxidation potential or 0.80 V or less, such as Na$_2$SO$_3$, NaHS, NaHSO$_3$, H$_3$P, H$_2$S, Na$_2$S, and Na$_2$S$_2$.

The reducing organic compounds include, for example, organic nitrogen compounds such as alkylamines and arylamines, organic sulfur compounds such as alkylmercaptans and arylmercaptans and organic phosphorus compounds such as alkylphosphines and arylphosphines, and in particular, compounds according to the Kendal-Pelz theory, are preferred.

Especially preferred reducing agents are described below.

3-Pyrazolidones and precursors thereof, such as 1-phenyl-3-pyrazolidone, 1-phenyl-4,4-dimethyl-3-pyrazolidone, 4-hydroxymethyl-4-methyl-1-phenyl-3-pyrazolidone, 1-m-tolyl-3-pyrazolidone, 1-p-tolyl-3-pyrazolidone, 1-phenyl-4-methyl-3-pyrazolidone, 1-phenyl-5-methyl-3-pyrazolidone, 1-phenyl-4,4-bis(hydroxymethyl)-3-pyrazolidone, 1,4-dimethyl-3-pyrazolidone, 4-methyl-3-pyrazolidone, 4,4-dimethyl-3-pyrazolidone, 1-(3-chlorophenyl)-4-methyl-3-pyrazolidone, 1-(4-chlorophenyl)-4-methyl-3-pyrazolidone, 1-(4-tolyl)-4-methyl-3-pyrazolidone, 1-(2-tolyl)-4-methyl-3-pyrazolidone, 1-(4-tolyl)-3-pyrazolidone, (1-(3-tolyl)-3-pyrazolidone, 1-(3-tolyl)-4,4-dimethyl-3-pyrazolidone, 1-(2-trifluoroethyl)-4,4-dimethyl-3-pyrazolidone, 5-methyl-3-pyrazolidone, 1,5-diphenyl-3-pyrazolidone, 1-phenyl-4-methyl-4-stearoyloxymethyl-3-pyrazolidone, 1-phenyl-4-methyl-4-lauroyloxymethyl-3-pyrazolidone, 1-phenyl-4,4-bis(lauroyloxymethyl)-3-pyrazolidone, 1-phenyl-2-acetyl-3-pyrazolidone, 1-phenyl-3-acetoxypyrazolione.

Hydroquinones and precursors thereof, such as hydroquinone, toluhydroquinone, 2,6-dimethylhydroquinone, t-tutylhydroquinone, 2,5-di-t-butylhydroquinone, t-octylhydroquinone, 2,5-di-t-octylhydroquinone, pentadecylhydroquinone, sodium 5-pentadecylhydroquinone-2-sulfonate, p-benzoyloxyphenol, 2-methyl-4-benzoyloxyphenol, 2t-butyl-4-(4-chlorobenzoyloxy)-phenol.

Various reducing agents and combinations thereof as illustrated in U.S. Pat. No. 3,039,869 may also be used in the present invention.

Color developers are usable as a reducing substance in the present invention, including p-phenylene-type color developers as described in U.S. Pat. No. 3,531,286. Among them, N,N-diethyl-3-methyl-p-phenylenediamine is typical. Other useful reducing agents include aminophenols as described in U.S. Pat. No. 3,761,270. Among the aminophenol reducing agents, especially useful compounds are 4-amino-2,6-dichlorophenol, 4-amino-2,6-dibromophenol, 4-amino-2-methylphenol sulfate, 4-amino-3-methylphenol sulfate, and 4-amino-2,6-dichlorophenol hydrochloride. Further, *Research Disclosure*, Vol. 151, RD No. 15108 (November 1976) and U.S. Pat. No. 4,021,240 describe 2,6-dichloro-4-substituted sulfonamidophenols and 2,6-dibromo-4-substituted sulfonamidophenols; and Japanese Patent Application (OPI) No. 116740/84 describes p-(N,N-dialkylaminophenyl)sulfamines; and these are usable in the present invention. In addition to the aforesaid phenol-type reducing agents, naphthol-type reducing agent such as 4-aminonaphthol derivatives and 4-substituted sulfonamidonaphthol derivatives as described in *Research Disclosure*, Vol. 178, RD No. 18742 (February, 1979) and Japanese Patent Application (OPI) No. 88136/81 are especially useful. Further, general color developers are usable in the present invention, which are described in various publications. For instance, U.S. Pat. No. 4,895,825 describes aminohydroxypyrazole derivatives; U.S. Pat. No. 2,892,714 describes aminopyrazoline derivatives; and *Research Disclosure*, Vol. 194, RD No. 19412 (June, 1980), pp. 227–230 and ibid., Vol. 194, RD No. 19415 (June, 1980), pp. 236–240 describe hydrazone derivatives. These color developers may be used singly or in the form of a combination of two or more thereof.

Where a non-diffusable reducing substance is included in the photosensitive material, the combined use of an electron transfer agent (ETA) is preferred for promoting electron transfer between the reducing substance and the developable silver halide emulsion.

The electron transfer agent (ETA) can be selected from among the reducing substances described earlier. The mobility of the electron transfer agent (ETA) should be greater than that of the immobile reducing substance in order to achieve the preferred effect of the ETA.

In such a case the reducing substance which is used conjointly with the ETA may be any of the aforementioned reducing agents, provided that it is essentially immobile in the layers of the photosensitive material, but the use of hydroquinones, aminophenols, aminonaphthols, 3-pyrazolidinones, saccharin and precursors thereof, picolinium salts, and the compounds disclosed as electron donors in Japanese Patent Application (OPI) No. 110827/78, etc. is preferred.

Examples of suitable reducing substance for jointly using with ETA's are shown below.

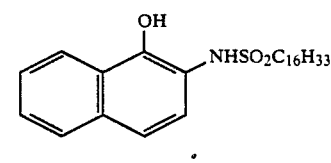
S-1

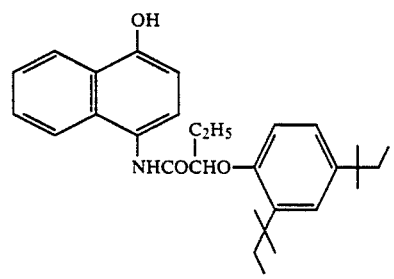
S-2

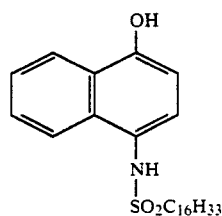
S-3

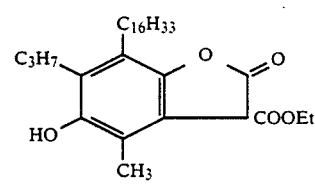
S-4

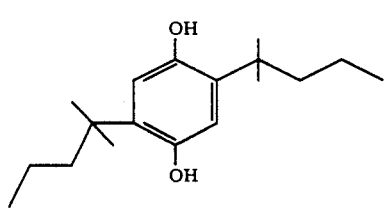
S-5

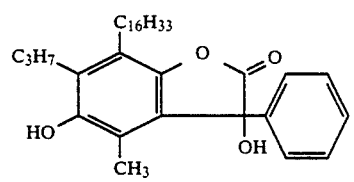
S-6

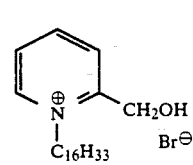
S-7

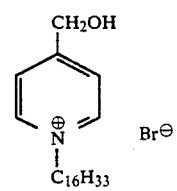
S-8

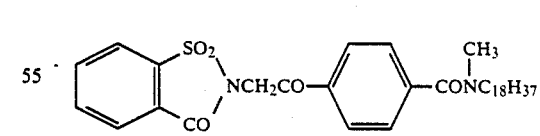
S-9

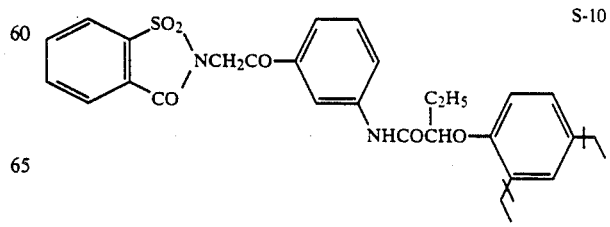
S-10

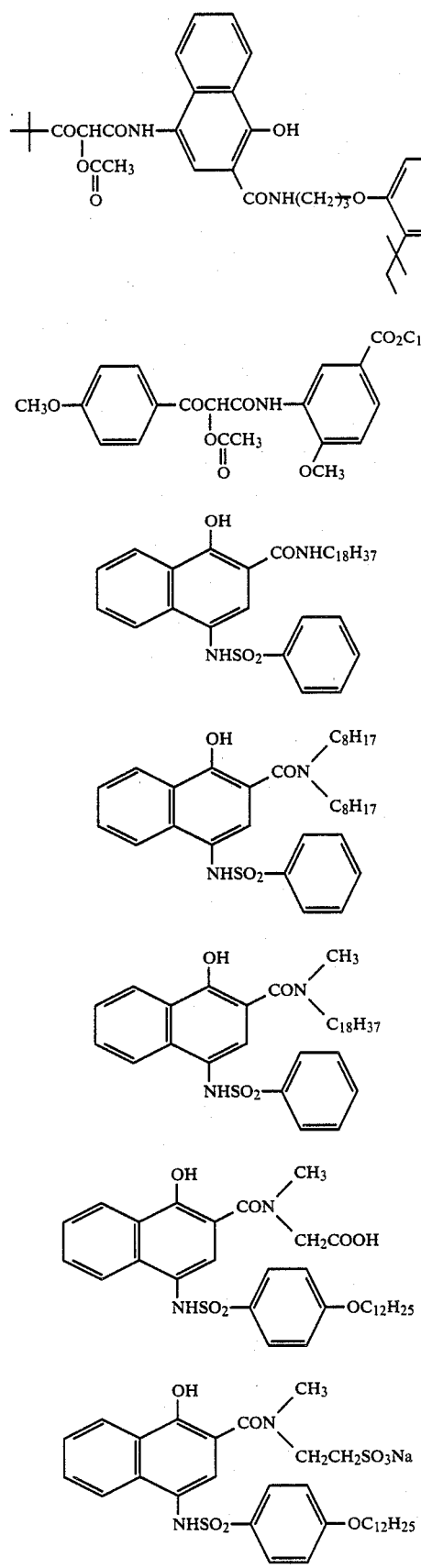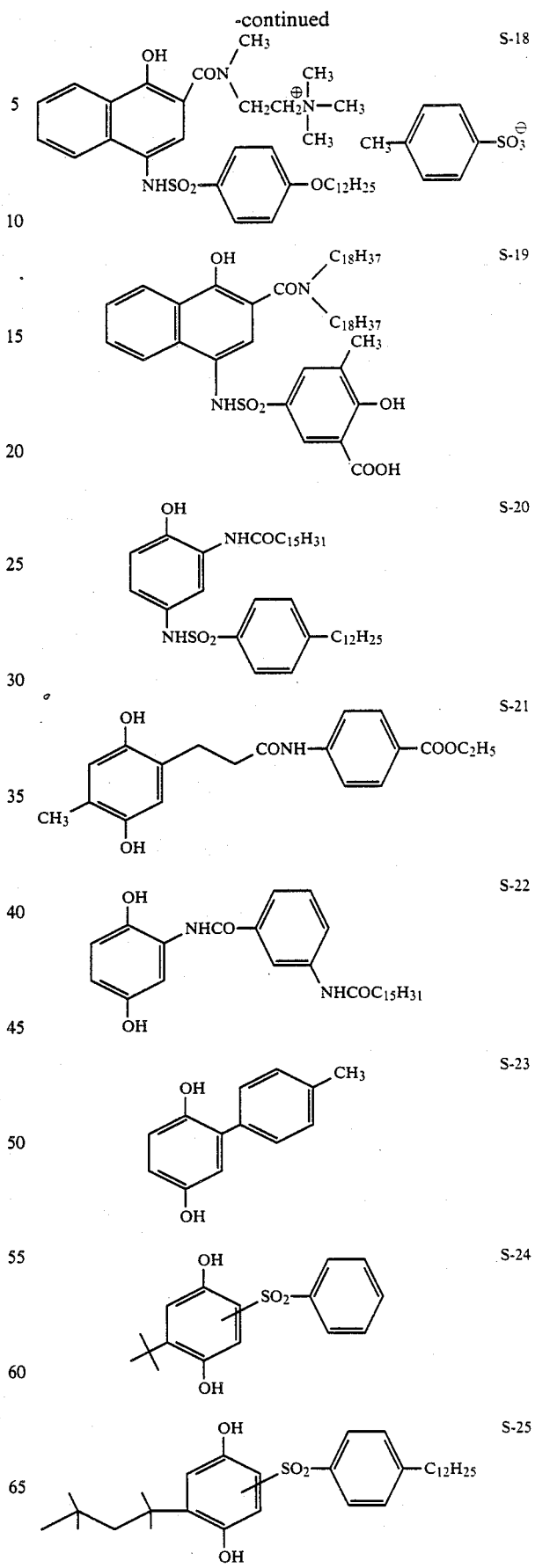

S-26

ETA's usable in combination with the reducing substance may be any ETA which may be cross-oxidized with the reducing substance. Preferred examples thereof are diffusible 3-pyrazolidines, aminophenols, phenylenediamines and reductones.

Specific examples include the following compounds: 3-pyrazolidinones such as 1-phenyl-3-pyrazolidinone, 4,4-dimethyl-1-phenyl-3-pyrazolidinone, 4-hydroxymethyl-4-methyl-1-phenyl-3-pyrazolidinone, 4-hydroxymethyl-4-methyl-1-tolyl-3-pyrazolidinone, 4-hydroxymethyl-4-methyl-1-(4'-methoxy)-3-pyrazolidinone, 4,4-bis(hydroxymethyl)-1-phenyl-3-pyrazolidinone, 4,4-bis(hydroxymethyl)-1-tolyl-3-pyrazolidinone, 4,4-bis(hydroxymethyl)-1-(4'-methoxy)-3-pyrazolidinone, 4,4-dimethyl-1-tolyl-3-pyrazolidinone, 1,5-diphenyl-3-pyrazolidinone; aminophenols such as p-aminophenol, p-methylaminophenol, p-dimethylaminophenol, p-dimethylaminophenol, p-dibutylaminophenol, o-piperidinoaminophenol, 4-dimethylamino-2,6-dimethoxy phenol; phenylenediamines such as N-methyl-p-phenylenediamine, N,N-dimethyl-p-phenylenediamine, N,N-diethyl-p-phenylenediamine, N,N,N',N'-tetramethyl-p-phenylenediamine, 4-diethylamino-2,6-dimethoxyaniline; and reductones such as piperidinohexose-reductone and pyrrolidinohexose-reductone.

In addition, precursors that can be hydrolyzed under alkaline conditions to form the aforesaid compounds may be used in the present invention. Such precursors are described, for example, in Japanese Patent Application (OPI) No. 52055/80, Japanese Patent Publication No. 39727/79 and Japanese Patent Application (OPI) No. 135949/82.

The compounds of formula (I) of the present invention may be used in conventional silver halide photographic materials which are to be developed with a developer near normal temperature (for example, X-ray films, lith films and other black-and-white photographic materials, color negative films, color papers, color reversal or other color photographic materials, color diffusion transfer photographic materials) and may also be used in other photographic materials for heat development.

When the present compounds are applied to conventional silver halide photographic materials, two systems are preferred for the reaction of the aforesaid reducing substance or the combination of the aforesaid reducing substance and ETA with the photographic material. In one system, the reducing substance or the combination of the substance and ETA is applied to the photographic material in the form of a developer in development thereof; and in the other system, the reducing substance is previously incorporated in the photographic material and the ETA is applied to the material in the form of a developer. In the former system, the preferred amount to be used is about 0.001 mole/liter to 1 mole/liter, which is the concentration of the substance(s) in the total developer solution. In the latter system of previous incorporation in the element, about 0.5 to 5 moles of the reducing substance is preferably incorporated into the material per mole of the present compound(s), and the concentration of ETA in the solution is preferably about 0.001 mole/liter to 1 mole/liter.

On the other hand, when the present compounds are applied to a heat developable photographic material, the reducing substance or the combination of the reducing substance and ETA is preferably previously incorporated into the heat developable photographic material. In this case, the preferred amounts are about 0.5 to 5 moles of the reducing substance and about 0.1 to 10 moles of ETA, per mole of the present compound(s).

The silver halide which can be used in the present invention may include any of silver chloride, silver bromide, silver iodide, silver chlorobromide, silver chloroiodide, silver iodobromide, and silver chloroiodobromide.

The halogen composition in the silver halide grains may be uniform, or the silver halide grains may have a multiple structure in which the composition is different between a surface portion and an inner portion, as disclosed in Japanese Patent Application (OPI) Nos. 154232/82, 108533/83, 48755/84 and 52237/84, U.S. Pat. Nos. 4,433,048 and European Patent 100,984, etc.).

Also, a tabular grain silver halide emulsion containing grains having a thickness of about 0.5 μm or less, a diameter of at least about 0.6 μm and an average aspect ratio of about 5 or more (see U.S. Pat. Nos. 4,414,310 and 4,435,499, and West German Patent Application (OLS) No. 3,241,646A1, etc.), and a monodisperse emulsion having a nearly uniform distribution of grain size see Japanese Patent Application (OPI) Nos. 178235/82, 100846/83 and 14829/83, PCT Application (OPI) No. 83/02338A1, and European Patents 64,412A3 and 83,377A1, etc.) may be used in the present invention.

Two or more kinds of silver halides in which the crystal habit, halogen composition, grain size and/or distribution of grain size, etc. are different may be used in mixture. Further, two or more kinds of monodisperse emulsions having different grain sizes from each other may be employed in mixture to control gradation.

The average grain size of the silver halide used in the present invention is preferably from about 0.001 μm to 10 μm, and more preferably from about 0.001 μm to 5 μm.

These silver halide emulsions can be prepared by any of an acid process, a neutral process, and an ammonia process. Further, a reaction system of soluble silver salts and soluble halogen salts may be any of a single jet process, a double jet process and a-combination thereof. In addition, a reverse mixing process in which silver halide grains are formed in the presence of an excess of silver ions, or a controlled double jet process in which the pAg in the liquid phase is kept constant, can also be utilized.

Moreover, for the purpose of increasing growth of grains, the concentration of addition, the amount of addition and/or rate of addition of silver salts and halogen salts added may be raised (see Japanese Patent Application (OPI) Nos. 142329/80 and 158124/80, and U.S. Pat. No. 3,650,757, etc.).

Furthermore, silver halide grains of epitaxial junction type (see Japanese Patent Applicaitoan (OPI) No.

16124/81, and U.S. Pat. No. 4,094,684, etc.) may be employed.

In the step for formation of silver halide grains used in the present invention, ammonia, an organic thioether derivative as described in Japanese Patent Publication No. 11386/72, or a compound containing sulfur as described in Japanese Patent Application (OPI) No. 14419/78, etc., can be used as a solvent for silver halide.

In a process of the formation or physical ripening of silver halide grains, a cadmium salt, a zinc salt, a lead salt, or a thallium salt, may coexist. These salts are used for the purposes of improving photographic pressure resistance. Further, for the purpose of eliminating high-intensity recoprocity failure or low-intensity reciprocity failure, a water-soluble iridium salt such as iridium (III or IV) chloride, ammonium hexachloroiridiate, etc. or a water-soluble rhodium salt such as rhodium chloride, etc., can be used.

Soluble salts may be removed from the silver halide emulsion after precipitate formation or physical ripening, and a noodle washing process or a flocculation process can be used for this purpose.

While the silver halide emulsion may be employed without being subject to after-ripening, it is usually chemically sensitized. For the chemical sensitization, a sulfur sensitization method, a reduction sensitization method, a noble metal sensitization method, etc., which are known in the field of emulsions for conventional photographic light-sensitive materials can be applied alone or in combination therewith. Such a chemical sensitization may be carried out in the presence of a nitrogen-containing heterocyclic compound (see Japanese Patent Application (OPI) Nos. 126526/83 and 215644/83, etc.).

The silver halide emulsion used in the present invention can be a surface latent image type in which a latent image is formed mainly on the surface of the grains, or an internal latent image type in which a latent image is formed mainly in the interior of the grains. Further, a direct reversal emulsion in which an internal latent image type emulsion and a nucleating agent are used in combination may be used. Examples of internal latent image type emulsions suitable for this purpose are described in U.S. Pat. Nos. 2,592,250 and 3,761,276, Japanese Patent Publication No. 3534/83, and Japanese Patent Application (OPI) No. 136641/82, etc. Preferred examples of the nucleating agents suitably used in the present invention are described in U.S. Pat. Nos. 3,227,552, 4,245,037, 4,255,511, 4,266,031 and 4,276,364, and West German Patent Application (OLS) No. 2,635,316, etc.

The silver halide used in the present invention can be spectrally sensitized with methine dyes or other dyes. Suitable dyes which can be employed include cyanine dyes, merocyanine dyes, complex cyanine dyes, complex merocyanine dyes, holopolar cyanine dyes, hemicyanine dyes, styryl dyes, and hemioxonol dyes. Of these dyes, cyanine dyes, merocyanine dyes and complex merocyanine dyes are particularly useful. Any conventional utilized nucleus for cyanine dyes is applicable to these dyes as a basic heterocyclic nucleus. That is, a pyrroline nucleus, an oxazoline nucleus, a thiazole nucleus, a selenazole nucleus, an aimidazole nucleus, a tetrazole nucleus, a pyridine nucleus, etc., and further, nuclei formed by condensing an alicylic hydrocarbon ring with these nuclei and nuclei formed by condensing an aromatic hydrocarbon ring with these nuclei, e.g., an indolenine nucleus, a benzindolenine nucleus, a benzoselenazole nucleus, a benzimidazole nucleus, a quinoline nucleus, etc., are appropriate. The carbon atoms of these nuclei may also be substituted.

The merocyanine dyes and complex merocyanine dyes may contain nuclei having a ketomethylene structure, 5- or 6-membered heterocyclic nuclei such as a pyrazolin -5-one nucleus, a thiohydantoin nucleus, a 2-thiooxazolidin-2,4-dione nucleus, a thiazolidin-2-dione nucleus, a rhodanine nucleus, a thiobarbituric acid nucleus, etc.

These sensitizing dyes can be employed individually, and can also be employed in combinations thereof. A combination of sensitizing dyes is often used, particularly for the purpose of supersensitization.

The sensitizing dyes may be present in the emulsion together with dyes which themselves do not give rise to spectrally sensitizing effects but which exhibit a supersensitizing effect or materials which do not substantially absorb visible light but which exhibit a supersensitizing effect. For example, aminostilbene compounds substituted with a nitrogen-containing heterocyclic group (for example, those described in U.S. Pat. Nos. 2,993,390 and 3,635,721, etc.), aromatic organic acid-formaldehyde condensates (for example, those described in U.S. Pat. No. 3,743,510, etc.), cadmium salts, azaindene compounds, etc., can be present. The combinations as described in U.S. Pat. Nos. 3,615,613, 3,615,641, 3,617,295 and 3,635,721 are particularly useful.

Gelatin is preferably used as the binder or protective colloid in the emulsion layers or intermediate layers of the present photographic materials, but other conventional hydrophilic colloids may be used alone or together with gelatin.

The gelatin may be either a lime treated gelatin or said treated gelatin in the present invention. Details on the preparation of gelatins are given in *The Macromolecular Chemistry of Gelatin*, written by Arther Vaise (Academic Press, 1964).

The photographic emulsions used in the present invention may contain surfactants singly or in the form of a mixture thereof.

These are essentially used as a coating auxiliary and sometimes for other purposes such as emulsification and dispersion, improvement of photographic characteristics for sensitization, static charge prevention and blocking prevention. These surfactants are classified into natural surfactants such as saponin; nonionic surfactants such as alkyleneoxide type, glycerin type or glycidol type surfactants; cationic surfactants such as higher alkylamines, quaternary ammonium salts, pyridine and the like heterocyclic compounds or phosphonium or sulfonium salts; anionic surfactants containing an acidic group such as a carboxylic acid, sulfonic acid, phosphoric acid, sulfate or phosphate group; and ampholytic surfactants such as amino acids, aminosulfonic acids or aminoalcohol sulfates or phosphates.

The photographic emulsions used in the present invention may contain various compounds for the purpose of the prevention of fog in manufacture, storage or photographic processing of the photographic materials or for the purpose of stabilization of photographic characteristics of the materials. For these purposes, various compounds which are known as anti-fogging agents or stabilizers may be used, including azoles such as benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (especially 1-phenyl-5-mercaptotetrazole); mercaptopyrimidines; mercaptotriazines; thioketo compounds such as oxazolinthione; azaindenes such as triazaindenes tetrazaindenes (especially 4-hydroxy-substituted (1,3,3a, 7-tetrazaindenes), pentazaindenes; as well as benzenethiosulfonic acid, benzenesulfinic acid and benzenesulfonic acid amide.

The photographic emulsion layers of the present photographic materials may contain, for the purpose of benzenesulfinic acid and benzenesulfonic acid amide.

The photographic emulsion layers of the present photographic materials may contain, for the purpose of increasing sensitivity, intensification of contrast or acceleration of development, for example, thioether compounds, thiomorpholines, quaternary ammonium salt compounds, urethane derivatives, urea derivatives, imidazole derivatives or 3-pyrazolidones.

The present photographic materials may further contain, in the photographic emulsion layers or in any other hydrophilic colloid layers, a water insoluble or sparingly soluble synthetic polymer dispersion for the purpose of the improvement of the dimensional stability of the material. Polymers usable for this purpose are homopolymers or copolymers of alkyl (meth) acrylates, alkoxyalkyl (meth)acrylates, glycidyl (meth)acrylates, (meth)acrylamides, vinyl esters (such as vinyl acetate), acrylonitriles, olefins and/or styrenes; as well as copolymers containing these monomers and other monomer components such as acrylic acid, methacrylic acid, $\alpha,\beta$-unsaturated dicarboxylic acids, hydroxyalkyl (meth)acrylates, sulfoalkyl (meth)acrylates and styrenesulfonic acids.

The present photographic materials may contain in the photographic emulsion layers, or in any other hydrophilic colloid layers, an inorganic or organic hardener. For example, chromium salts (such as chromium alum, chromium acetate), aldehydes (such as formaldehyde, glyoxal, glutaraldehyde), N-methylol compounds (such as dimethylolurea, methyloldimethylhydantoin), dioxane derivatives (such as 2,3-dihydroxydioxane), active vinyl compounds (such as 1,3,5-triacryloyl-hexahydro-s-triazine, 1,3-vinylsulfonyl-2-propanol), active halogen-containing compounds (such as 2,4-dichloro-6-hydroxy-s-triazine), mucohalogenic acids (such as mucochloric acid, mucophenoxychloric acid) and like hardeners may be used singly or in the form of a combination thereof.

The silver halide photographic materials of the present invention may contain other conventional additives well known in the art, for example, whitening agents, dyes, desensitizers, coating assistants, antistatic agents, plasticizers, sliding agents, matting agents, development accelerators, mordanting agents, ultraviolet light absorbents, discoloration inhibitors and color fog-prevention agents.

Examples of such additives which may be used in the present invention are disclosed, for example, in *Research Disclosure*, Vol. 176, RD No. 17643 (December, 1978), pp. 22–31.

Various color couplers may be used in the present photographic materials. "Color couplers" as used herein mean compounds capable of forming dyes by a coupling reaction with an oxidized aromatic primary amine developing agent. Typical examples of usable color couplers are naphthol or phenol type compounds, pyrazolone or pyrazoloazole type compounds and open or heterocyclic ketomethylene compounds. Examples of cyan, magenta and yellow couplers which may be used in the present invention are described in the patent publications referred to in *Research Disclosure*, Vol. 176, RD No. 17643 (December, 1978), item VII-D and ibid., Vol. 187, RD No. 18717 (November, 1979).

The color couplers incorporated in the photographic materials of this invention are preferably non-diffusible and have a ballast group or are polymerized. Two-equivalent couplers (where the coupling splite-off group is substituted) are preferred to four-equivalent couplers (where the coupling active site has a hydrogen atom), because the amount of the silver coated is reduced. Further, couplers capable of forming a dye with a diffusible, non-coloring coupler, a DIR coupler capable of releasing a development inhibitor on coupling or a coupler capable of releasing a development accelerator on coupling may also be used.

Typical yellow couplers used in the present invention are oil protected acylacetamide couplers. Examples are described, e.g., in U.S. Pat. Nos. 2,407,210, 2,875,057 and 3,265,506. Two-equivalent yellow couplers are preferably used in the present invention, and examples are oxygen atom-releasing type yellow couplers as described in U.S. Pat. Nos. 3,408,194, 3,447,928, 3,933,501, and 4,022,620; and nitrogen atom-releasing type yellow couplers as described in Japanese Patent Publication No. 10739/83, U.S. Pat. Nos. 4,401,752 and 4,326,024, *Research Disclosure*, Vol. 180, RD No. 18053 (April 1979) British Patent 1,425,020 and German Patent (OLS) Nos. 2,219,917, 2,261,361, 2,329,587, and 2,433,812. The $\alpha$-pivaloylacetanilide type couplers are excellent in the fastness of the colored dyes, in particular in the light fastness thereof, and the $\alpha$-benzoylacetanilide type couplers generally form dyes of high color density.

The magenta couplers which may be used in the present invention are oil protected type indazolone or cyanoacetyl couplers, especially 5-pyrazolone type or pyrazoloazole type couplers, such as pyrazolotriazoles. Among the 5-pyrazolone type couplers, those in which the 3-position is substituted by an arylamino group or an acrylamino group are preferred in view of the hue or the color density of the colored dyes; typical examples thereof are described in U.S. Pat. Nos. 2,311,082, 2,343,703, 2,600,788, 2,908,573, 3,062,653, 3,152,896, and 3,936,015. As the releasing group in the two-equivalent 5-pyrazolone type couplers, preferred are the nitrogen atom-releasing groups as described in U.S. Pat. No. 4,310,619 and the arylthio groups as described in U.S. Pat. No. 4,351,897. The 5-pyrazolone type couplers with a ballast group as described in European Patent 73,636 also can form dyes with a high color density and are useful herein.

Examples of pyrazoloazole type couplers useful herein are pyrazolobenzimidazoles as described in U.S. Pat. No. 3,061,432, preferably pyrazole(5,1-c)(1,2,4) triazoles as described in *Research Disclosure*, Vol. 242, RD No. 24220 (June, 1984) and Japanese Patent Application (OPI) No. 33552/85; and pyrazolopyrazoles as described in ibid., Vol. 242, RD No. 24230 (June, 1984) and Japanese Patent Application (OPI) No. 43659/85. Imidazo(1,2-b) pyrazoles as described in U.S. Pat. No. 4,500,630 are preferable because of the lower yellow side absorption of the colored dyes and the light fastness thereof, and in particular, pyrazolo-(1,5-b)(1,2,4)triazoles as described in U.S. Pat. No. 4,540,654 are especially preferred.

Cyan couplers which may be used in the present invention are oil protected type naphthol and phenol couplers; typical examples thereof are naphthol type couplers as described in U.S. Pat. No. 2,474,293, especially oxygen atom-releasing type two-equivalent naphthol couplers as described in U.S. Pat. Nos. 4,052,212, 4,146,396, 4,228,233 and 4,296,200. Examples of phenol type couplers are given in, e.g., U.S. Pat. Nos. 4,369,929, 2,801,171, 2,772,162, and 2,895,826. Cyan couplers which are resistant to moisture and temperature are preferably used in the present invention, and typical examples thereof are phenol type cyan couplers having an ethyl or higher alkyl group in the m-position of the phenol nucleus, as described in U.S. Pat. No. 3,772,002; 2,5-diacylamino substituted phenol type couplers, as described in U.S. Pat. Nos. 2,772,162, 3,758,308, 4,126,396, 4,334,011, and 4,327,173, German Patent (OLS) No. 3,329,729 and European Patent 121,365; and phenol type couplers having a 2-phenylureido group and a 5-acylamino group, as described in U.S. Pat. Nos. 3,446,622, 4,333,999, 4,451,559, and 4,427,767. In addition, naphthol type cyan couplers having a sulfonamido or amido group in the 5-position of the naphthol nucleus thereof, as described in Japanese Patent Application (OPI) No. 237448/85 and European Patent 161,626, can preferably be used in the present invention, to form color images of high fastness.

In order to correct unnecessary absorption of dyes formed from the magenta and cyan couplers in the short wavelength region, colored couplers are preferably used in color negative photographic materials for photographing. Typical examples of colored couplers are yellow colored magenta couplers as described in U.S. Pat. No. 4,163,670 and Japanese Patent Publication No. 39413/82; and magenta colored cyan couplers as described in U.S. Pat. Nos. 4,004,929 and 4,128,258 and British Patent 1,146,368.

Couplers forming dyes with an appropriate diffusibility may be used for an improvement of graininess. Regarding smearing couplers, examples of magenta couplers are described in U.S. Pat. No. 4,366,237 and British Patent 2,125,570; and yellow, magenta or cyan couplers are described in European Patent 96,570 and German Patent (OLS) No. 3,234,533.

The dye forming couplers and the aforesaid special couplers may form dimers or higher polymers. Typical examples of polymerized dye forming couplers in general are described in U.S. Pat. Nos. 3,451,820 and 4,080,211. Examples of polymerized magenta couplers are described in British Patent 2,102,173, U.S. Pat. No. 4,367,282 and U.S. patent application Ser. Nos. 849,589 (filed Apr. 8, 1986) and 866,833 (filed May 27, 1986).

Regarding the incorporation of various kinds of couplers into the photographic materials in the present invention, two or more different kinds of couplers may be added to one light-sensitive layer, or the same coupler may be added to two or more different layers.

The compounds of the present invention may be used together with couplers, and may be added to the same emulsion layer together with the couplers, or may be added to an intermediate layer(s) or another photographic auxiliary layer(s) in the form of an independent emulsified dispersion.

The amount of the present compounds to be used is about 0.1 to 50 mol%, preferably about 0.3 to 15 mol%, based on the coupler in each light-sensitive layer, or the yellow coupler in the blue-sensitive layer, the magenta coupler in the green-sensitive layer or the cyan coupler in the red-sensitive layer, in the color photographic material. The amount is preferably about $1 \times 10^{-5}$ mole to $8 \times 10^{-2}$ mole, especially about $1 \times 10^{-4}$ mole to $5 \times 10^{-2}$ mole, per mole of the silver halide in the layer to which the present compound is to be added.

In the case the silver halide photographic materials of the present invention are processed by a conventional wet method, any and every conventional means by be use. Known processing solutions may be used. The processing temperature is generally selected in the range of about 18° C. to 50° C., but this may be lower than 18° C. or higher than 50° C. In accordance with the desired use of the photographic materials, any black-and-white photographic processing for development for the formation of silver images or color photographic processing for development for the formation of color images may be applied to the materials.

Details on various useful photographic processing procedures are described in T. H. James, 4th Ed., *The Theory of the Photographic Process*, pp. 291-436, and *Research Disclosure*, Vol. 176, RD No. 17643 (December, 1978), pp. 28-30.

For fixing after black-and-white development, conventional fixers of general compositions may be used. The fixers may contain a thiosulfate or thiocyanate as a fixing agent or an organic sulfur containing compound which is known to be effective as a fixing agent. The fixer may contain a water-soluble aluminum salt as a hardener.

After color development, the photographic emulsion layers are generally bleached. The bleaching may be carried out simultaneously with fixing or separately therefrom.

As the bleaching agent there may be used polyvalent metal compounds such as iron (III), cobalt (III), chromium (VI) or copper (II) compounds, peracids, quinones or nitroso compounds. For instance, ferricyanides, bichromates and iron (III) or cobalt (III) organic complexes, for example, with an organic acid such as an aminopolycarboxylic acid (e.g., ethylenediaminetetraacetic acid, nitrilotriacetic acid, 1,3-diamino-2-propanoltetraacetic acid), citric acid, tartaric acid or malic acid; persulfates and permanganates; and nitrosophenols, etc., may be used. In particular, potassium ferricyanide, sodium ethylenediaminetetraacetate iron (III) and ammonium ethylenediaminetetraacetate iron (III) are especially useful. Ethylenediaminetetraacetate iron (III) complexes are useful either in an independent bleaching solution or in a combined bleach-fix bath.

The bleaching or bleach-fixing solution may contain various additives such as a bleach accelerator as described in U.S. Pat. Nos. 3,042,520 and 3,241,966 and thiol compound as described in Japanese Patent Application (OPI) No. 65732/78.

Heat developable photosensitive materials which provide a colored image are within the scope of the invention, as well as heat developable photosensitive materials with which a silver image is obtained as described on pages 242-255 of *Fundamentals of Photographic Engineering* (Japanese), non-silver salt photography edition (1982, published by Corona Co.); page 40 of the April 1979 edition of *Eizo Joho*; pages 32-33 of Nebletts, "Handbook of Photography and Reprography" 7th Edition, (published by the Van Nostrand Reinhold Co.); U.S. Pat. Nos. 3,152,904, 3,301,678, 3,392,020 and 3,457,075, British Patents 1,131,108 and 1,167,777, and on pages 9-15 of *Research Disclosure*, RD No. 17029 (June, 1978). Heat developable photosensitive materials for providing colored images have been disclosed in U.S. Pat. Nos. 3,531,286 and 3,761,270. Belgian Patent No. 802,519, on pages 31, 32 of *Research Disclosure*, September, 1975, and in U.S. Pat. Nos. 4,021,240, 4,463,079, 4,474,867, 4,478,927, 4,507,390, 4,500,626 and 4,483,914, Japanese Patent Application (OPI) Nos. 149046/83, 149047/83, 152440/84, 15445/84, 165054/84, 180548/84, 168439/84, 174832/84, 174833/84, 174834/84, 174835/84, etc., U.S. Pat. No. 4,499,180, Japanese Patent Application (OPI) No. 116943/84, European Patent 125521, U.S. Pat. No. 4,499,172 and Japanese Patent Application (OPI) Nos. 180537/84, 84640/86, 218443/84 and 238056/86, and the invention can also be applied to the heat developable color photosensitive materials disclosed in European Patent Document (Laid-Open) No. 210,660.

The compounds of this invention can be used in the silver halide photographic materials for the color diffusion transfer process, which are developed using a processing liquid at a temperature close to room temperature. A color diffusion transfer method has been disclosed, for example, in Belgium Patent No. 757,959.

The invention is now illustrated in greater detail with reference to specific examples, but the invention is not to be construed as being limited thereto.

EXAMPLE 1

(1) Preparation of a Photosensitive Silver Halide Emulsion

Thick tabular silver iodobromide grains (AgI content 4 mol%) of average grain size 1μ were prepared by adding potassium bromide and potassium iodide along with silver nitrate to an aqueous % gelatin solution with vigorous agitation. Subsequently, the emulsion was washed with water using the normal precipitation method. Then the emulsion was chemically sensitized using gold and sulfuric acid sensitization with chloroauric acid and sodium thiosulfate to provide the photosensitive silver iodobromide emulsion A.

(2) Preparation of a Coated Samples

Samples 1 to 8 were prepared by coating the layers indicated below successively from the support side on a triacetylcellulose support thick.

The additives other than the emulsion in the emulsion layer and the surface protecting layer were as indicated below.

| Emulsion Layer | |
|---|---|
| Binder: Gelatin | 1.6 g per gram of silver |
| Coated silver weight | 1.1 g/m² |
| Sensitizing dye | 2.1 mg per gram of silver |

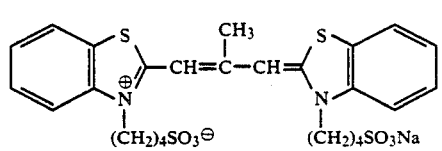

| Coating Promoters: | |
|---|---|
| Sodium dodecylbenzenesulfonate | 0.1 mg/m² |
| Poly(potassium p-styrenesulfonate) | 1 mg/m² |
| Surface Protecting Layer | |
| Binder: Gelatin | 0.7 g/m² |
| Coating Promoters: | 0.2 mg/m² |
| Sodium N-oleoyl-N-methyltaurate | |
| Matting Agent: | 1.13 mg/m² |
| Fine poly(methyl methacrylate) particles (average particle size; 3 μm) | |
| Film Hardening Agent: | see Table 1 |
| Compound of the Invention: | see Table 1 |

(3) Sensitometry

These samples were stored for 7 days after coating, under conditions of 25° C., 65% RH. Each sample was then developed for 7 minutes at 20° C. in the development bath indicated below, fixed, washed with water and dried, and the image storage properties were evaluated. (The water washing times were as indicated in Table 1.)

The wet scratch strengths were measured in the development bath.

| Development Bath | |
|---|---|
| Metol | 2 g |
| Sodium sulfite | 100 g |
| Hydroquinone | 5 g |
| Borax deca-hydrate | 2 g |
| Water to make | up to 1 liter |
| Fixing Bath | |
| Ammonium thiosulfate | 240.0 g |
| Sodium sulfite (anhydrous) | 15.0 g |
| Acetic acid (28%) | 48 ml |
| Sodium metaborate | 15 g |
| Potassium alum | 15 g |
| Water to make | up to 1.0 liter |

(a) Image Storage Properties

The processed and dried samples were stored for 3 days under conditions of 80° C., 70% RH and then they were evaluated to determine the extent of the loss of optical density compared to an original optical density of 1.0.

O: Good

Δ: Some reduction in density but within practical tolerance

X: Marked reduction in density, outside practical tolerance (b) Wet Scratch Strength Each samples was withdrawn from the development bath after 4 minutes at 20° C. before development was complete and scratched with a needle of radium 0.5 mm under a gradually increasing load. The evaluation was made on the basis of the load at which scratching occurred.

TABLE 1

| Sample | Compound | Hardening Agent | Washing Time | Image Storage Properties | Wet Starch Strength |
|---|---|---|---|---|---|
| 1 (Comparative Example) | None | 8 mg/m² | 1 min. 5 | X Δ | 90 g |
| 2 (This Invention) | Compound 22 3 mg/m² | 5 mg/m² | 1 5 | Δ O | 90 g |
| 3 (This Invention) | Compound 22 5 mg/m² | 3 mg/m² | 1 5 | O O | 91 g |
| 4 (This Invention) | Compound 14 3 mg/m² | 5 mg/m² | 1 5 | O O | 92 g |
| 5 (This Invention) | Compound 14 5 mg/m² | 3 mg/m² | 1 5 | O O | 90 g |
| 6 (Comparative Example) | None | 5 mg/m² | 1 5 | O O | 42 g |

Hardening Agent: 1,2-Bis(vinylsulfonylacetamido)ethane

It is clear that Samples 2 to 5, which contained compounds of this invention, had better image storage properties and wet scratch strength than Comparative Examples 1 and 6.

While the invention has been described in detail and with reference to specific embodiments thereof, it will be apparent to one skilled in the art that various changes and modifications can be made therein without departing from the spirit and scope thereof.

What is claimed is:

1. A silver halide photographic material comprising a support having thereon at least one light-sensitive silver halide emulsion layer, at least one layer of said material comprising gelatin crosslinked with a crosslinking agent, wherein said crosslinks are cleaved on reduction, and wherein said crosslinking agent is represented by formula (I):

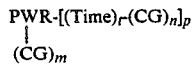

PWR-[(Time)$_t$—(CG)$_n$]$_p$ (I)
|
(CG)$_m$ wherein PWR represents a group capable of releasing ${(Time)_t—(CG)_n}_p$ on reduction; Time represents a group capable of releasing —(CG)$_n$ after —[(Time)-$_t$—(CG)$_n$]$_p$ is released from PWR; CG represents a group capable of bonding with gelatin; n, m, and p each is an integer of 1 to 3; and t is 0 or 1.

2. The silver halide photographic material as claimed in claim 1, wherein PWR is represented by formula (II):

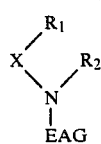

(II)

wherein X represents an oxygen atom, a sulfur atom or a group —N(R$_3$)—; EAG represents an aromatic group capable of accepting at least one electron from a reducing substance; R$_1$, R$_2$ and R$_3$, which may be the same or different, each represents a substituted or unsubstituted alkyl group, a substituted or unsubstituted aralkyl group, a substituted or unsubstituted alkenyl group, a substituted or unsubstituted alkynyl group, a substituted or unsubstituted aryl group, a substituted or unsubstituted heterocyclic group, a substituted or unsubstituted acyl group, a substituted or unsubstituted sulfonyl group, a substituted or unsubstituted carbamoyl group, or a substituted or unsubstituted sulfamoyl group; provided that any of R$_1$, R$_2$, R$_3$ and EAG may be linked to form a 3-membered to 8-membered ring, at least one of R$_1$, R$_2$, R$_3$ and EAG is bonded to —[(Time)$_t$—(CG)$_n$]$_p$, at least one of R$_1$, R$_2$, R$_3$ and EAG is bonded to —(CG)$_m$, and R$_1$, R$_2$ and R$_3$ may each represent a single bond to —[(Time)$_t$—(CG)$_n$]$_p$ or —(CG)$_m$.

3. The silver halide photographic material as claimed in claim 2, wherein PNR is represented by formula (III):

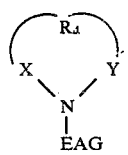

(III)

wherein Y represents a divalent linking group; R$_4$ represents an atomic group necessary for forming a 5-membered to 8-membered heterocyclic ring or a 5-membered to 8-membered condensed heterocyclic ring; and X and EAG each is as defined in formula (II).

4. The silver halide photographic material as claimed in claim 3, wherein said divalent linking represented by Y

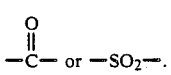

5. The silver halide photographic material as claimed in claim 2, wherein EAG is represented by formula (A)

(A)

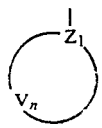

wherein $Z_1$ represents

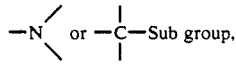

V represents an atomic group necessary for forming a 3-membered to 8-membered aromatic ring containing members selected from

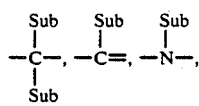

[—N—]—N=, —O—, —S— and —SO₂—, wherein Sub represents a hydrogen atom or a substituent, and plural Sub groups may be the same or different, and at least two Sub groups may be linked to form a 3-membered to 8-membered saturated or unsaturated carbon ring or a 3-membered to 8-membered saturated or unsaturated heterocyclic ring; provided that the sum of the Hammett's constants $\sigma_{para}$ of said Sub group is at least +0.50.

6. The silver halide photographic material as claimed in claim 5, wherein EAG represents a heterocyclic group substituted with at least one electron-withdrawing group or an aryl group substituted with at least one electron-with-drawing group.

7. The silver halide photographic material as claimed in claim 1, wherein Time represents a group capable of releasing —(CG)$_n$ after the cleavage of a nitrogen-oxygen, nitrogen-nitrogen or nitrogen-sulfur bond in PWR.

8. The silver halide photographic material as claimed in claim 1, wherein CG is selected from the group consisting of —X'—CO—CH₂—Y' (wherein X' represents a single bond or —O—; and Y' represents an electron withdrawing group, for example, —CN, —COCH₃,

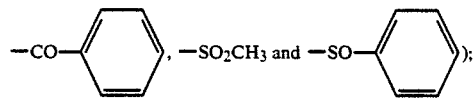

—SO₂CH=CH₂; —SO₂CH₂CH₂X²; (wherein X² represents a group released by substitution reaction or elimination reaction upon reacting the group of formula (3) with a nucleophilic reagent or base, for example, —Cl—, —OSO₂CH₃,

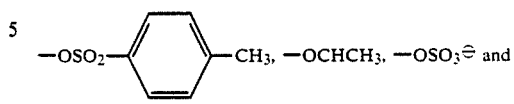

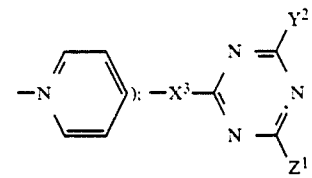

(wherein X³ represents a single bond, —O—, —N(R)— (wherein R represents hydrogen atom, alkyl group, and aralkyl group), Y² and Z¹ each represents halogen atom (such as Cl or Br), hydroxy group and salt thereof, substituted or unsubstituted amino group, provide that at least one of Y² and Z¹ is halogen atom); —CHO;

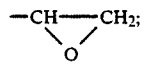

—NCO; —NHCONHCOCH;50 CH₂; —NHCONH-CO—CH₂CH₂—X² (wherein X² means the same as defined above); —COX⁴ (wherein X⁴ is a group capable of being easily released upon reacting a functional group in formula (10) with an amino group of gelatin, for example, —Cl,

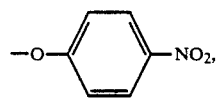

—O—CH₂, —CN, succinimido-1-yloxy group, 2-pyridyloxy group); and

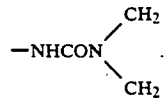

9. The silver halide photographic material as claimed in claim 1, wherein said crosslinking agent is present in an amount of at least about 0.1 mmol/m² of said photographic material.

10. The silver halide photographic material as claimed in claim 9, wherein said crosslinking agent is present in an amount of from about 1 mmol/m² to 400 mmol/m² of said photographic material.

* * * * *